Figure 1:
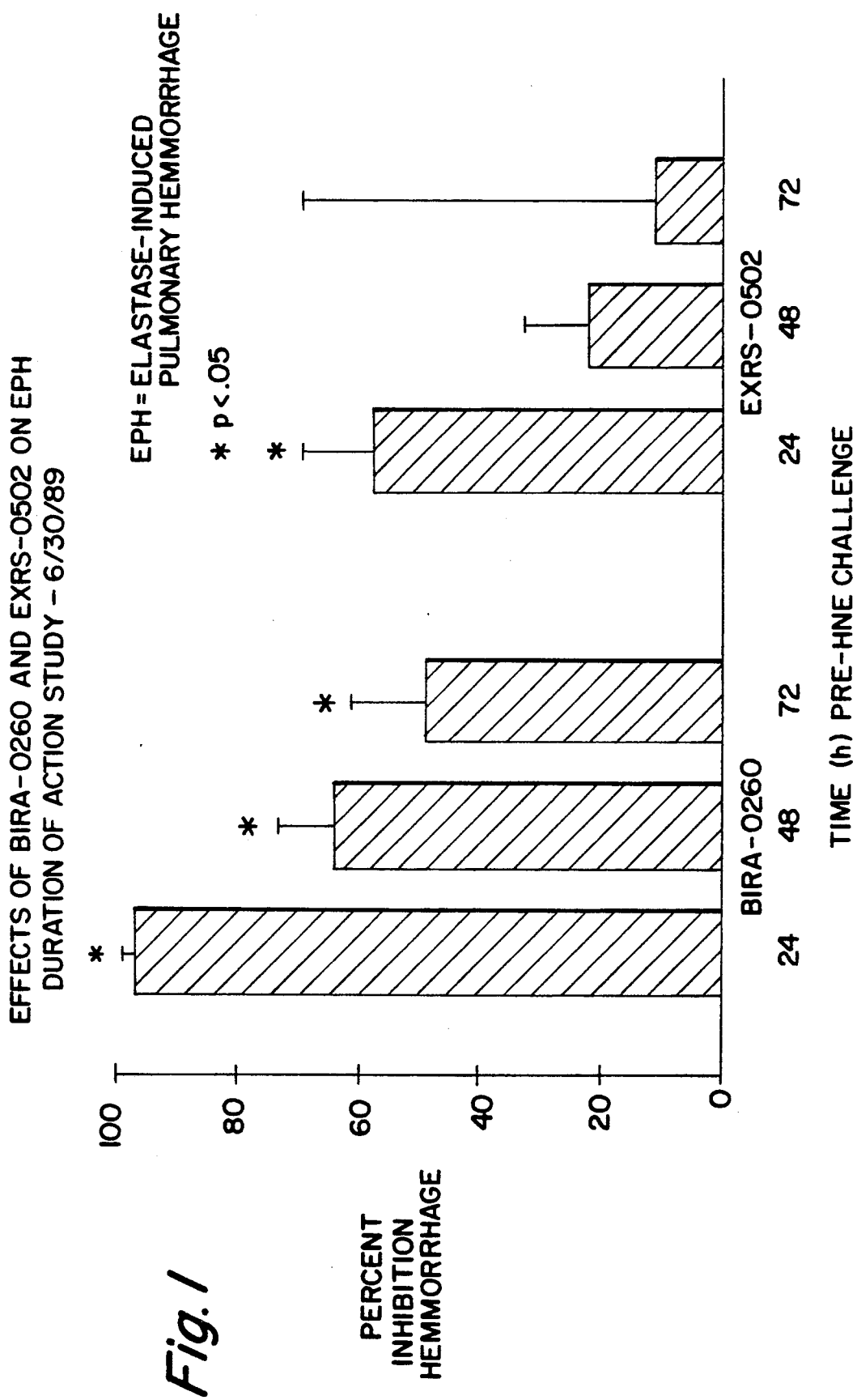

United States Patent [19]

Skiles

[11] Patent Number: 5,221,665
[45] Date of Patent: Jun. 22, 1993

[54] N-SUBSTITUTED AMIDES

[75] Inventor: Jerry W. Skiles, Brookfield, Conn.

[73] Assignee: Boehringer Ingelheim Pharmaceuticals, Inc., Ridgefield, Conn.

[21] Appl. No.: 686,918

[22] Filed: Apr. 16, 1991

Related U.S. Application Data

[63] Continuation of Ser. No. 426,069, Oct. 27, 1989, abandoned.

[51] Int. Cl.$^5$ .................. A61K 37/02; C07K 5/10; C07K 7/06
[52] U.S. Cl. ........................... 514/18; 514/17; 530/330
[58] Field of Search .............. 514/17, 18; 530/330

[56] References Cited

U.S. PATENT DOCUMENTS

| | | | |
|---|---|---|---|
| 4,873,221 | 10/1989 | Trainor | 514/18 |
| 4,880,780 | 11/1989 | Trainor et al. | 514/18 |
| 4,910,190 | 3/1990 | Bergeson et al. | 514/19 |
| 4,923,890 | 5/1990 | Trainor et al. | 514/11 |

FOREIGN PATENT DOCUMENTS 0276101  1/1988  European Pat. Off. .

OTHER PUBLICATIONS

Stein et al., "Mechanism of Slow Binding Inhibition of HLE by Trifluoromethyl Ketones", Biochem. (1987) 26, pp. 2682–2689.

*Primary Examiner*—Lester L. Lee
*Attorney, Agent, or Firm*—D. E. Frankhouser; A. R. Stempel; M-E. M. Timbers

[57] ABSTRACT

N-substituted amides which inhibit hydrolysis of elastin, are described, which compounds are tri-and di- fluoromethyl ketone amide and non-naturally occurring n-substituted amino acids derivatives.

3 Claims, 1 Drawing Sheet

N-SUBSTITUTED AMIDES

This is a continuation of application Ser. No. 426,069, filed Oct. 27, 1989, and now abandoned.

BACKGROUND OF THE INVENTION

All multicellular organisms comprise material with tensile strength and rigidity, such as bone and collagen, to maintain shape and to facilitate mechanical movement. Additionally, however, such organisms also must comprise a component with intrinsic elasticity, a component that can stretch and then undergo elastic recoil when required. For warm-blooded animals, this elasticity component is an unusual fibrous protein, elastin. Although elastin is present in virtually all tissue in some animals, it comprises an appreciable percentage of all protein in only some tissues, such as the arteries, some ligaments and the lungs. The elastin content of the human lung is about 28%.

Elastin can be hydrolized or otherwise destroyed by a select group of enzymes classified as elastases. The elastases are derived from many tissues in man, including the pancreas, neutrophils, macrophages, monocytes, platelets, smooth muscle cells and fibroblasts. Although called elastases, these enzymes are not just elastin-specific, and have been shown to cleave other proteins.

The role of elastases in normal elastin metabolism is difficult to assess, but a role in protein turnover is assumed. Human neutrophil granulocytes are the source of the neutral protease, human leukocyte elastase (HLE). HLE is a protease capable of hydrolysing most connective tissue components. However, its most likely primary physiologic substrate is elastin. Since destruction of elastin and the concomitant loss of elastic recoil in the emphysematous lung have been well established, HLE has been postulated to be the primary destructive agent in the pathogenesis of emphysema. Increased proteolysis, especially elastolysis, may occur in the lung parenchyma as a result of an imbalance between HLE and its major inhibitor, alpha-1-protease inhibitor, either because of an increased release of the enzyme in the lung or because of an acquired or inherited deficiency of the protease inhibitor. Cigarette smoke, which has been shown to oxidatively inactivate alpha-1-protease inhibitor in vitro, is believed to cause a localized functional deficiency of the protease inhibitor in the lungs of smokers. This breakdown of the antiprotease shield in lungs is thought to be a primary factor in the pathogensis of centrilobular emphysema associated with cigarette smoking.

Recently, certain trifluoromethyl ketone substituted peptide derivatives have been published, which derivatives are stated to be inhibitors of HLE. EP Appln. No. 86300379.4 (Publication No. 0189305-Jul. 30, 1986).

THE INVENTION

This invention relates to new chemical compounds having valuable pharmaceutical activity. In particular the present invention relates to certain tri- and di- fluoromethyl ketone amide derivatives which are inhibitors of HLE, which property makes such compounds useful whenever such inhibition is desired. For example, such compounds may be useful in the treatment of tissue degenerative diseases. Additionally, such compounds may serve as diagnostic aids. Accordingly, such inhibitors could be used in the diagnosis and treatment of pulmonary emphysema, rheumatoid arthritis, osteoarthritis, and arteriosclerosis, among other diseases.

The substituted amides of the present invention may be represented by the following formulae:

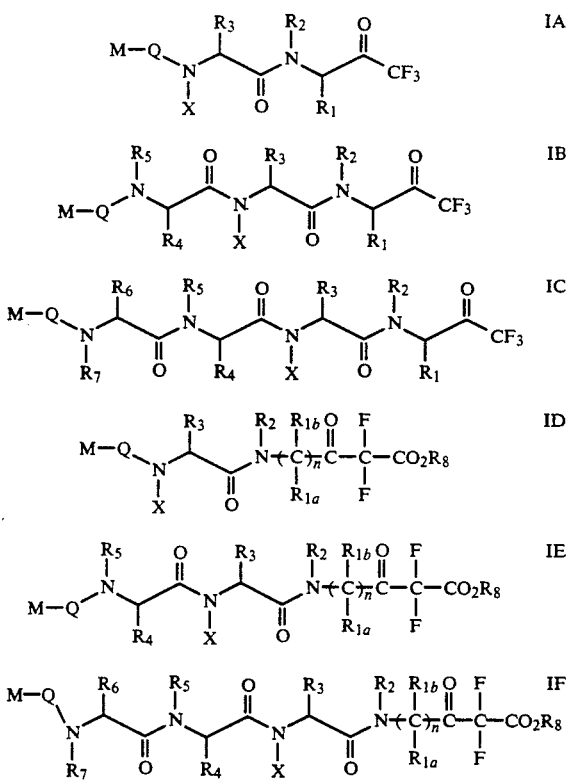

wherein $R_{1a}$, $R_{1b}$, $R_3$, $R_4$, and $R_6$ are each selected independently from hydrogen, lower alkyl, substituted alkyl, aryl, aralkyl, substituted aralkyl, substituted aryl or the side chains of naturally occurring alpha-amino acids. $R_1$, $R_{1a}$, $R_{1b}$, $R_3$, $R_4$, and $R_6$ may be lower alkyl groups containing from 1 to 12 carbons and may be substituted by the following groups: hydroxy; amino; alkoxy; alkenyl; alkynyl; alkylamino containing from 1 to 6 carbons; dialkylamino wherein each alkyl group contains from 1 to 6 carbons; mercapto; thioakyl; alkanoyl containing from 1 to 6 carbons; arylcarbonyl wherein the aryl group contains 6, 10 or 12 carbons; aralkanonyl containing 8 to 13 carbons; amido which may be attached to the alkyl group via either the nitrogen or carbon of the amido; guanidino; carboxy; carboxyalkyl; cycloalkyl (3-15 carbons); cycloalkylalkyl (4-12 carbons); aryl or heteroaryl which may optionally be partially hydrogenated ; heteroalkyl; heteroarylalkyl; aryl containing 6, 10 or 12 carbons; bicycloalkyl; bicycloalkyl-alkyl; alkylureido; aralkylureido; arylureido; indanyl;

$R_2$, $R_5$ and $R_7$ are each independently hydrogen, lower alkyl, (1-6 carbons), cycloalkyl (3-9 carbons), cycoalkylalkyl (4-12 carbons), aralkyl, aryl, or X;

$R_8$ is hydrogen, lower alkyl, aralkyl, naturally occurring amino acids, $NH(C)_nR_1R_2COOR$ where $R_1$ and $R_2$ are as described above and R is hydrogen and n is as described below, lower alkyl, aralkyl, or $NR_1R_2$. When $R_8$ is a naturally occurring alpha amino acid it will be appreciated by those skilled in the art that in the cases of bi-functional amino acid such as ornithine, lysine, and the like, that bear two amino functionalities that yield amide bond formation to give ID, IE, or IF may occur via the alpha amino functionality or via the side chain amino functionality. Both types of compounds are within the scope of this invention;

n is an integer, 1 or 2;

X is hydrogen, lower alkyl, cycloalkyl, aryl, bicycloalkyl, heteroaryl, alkenyl, alkynyl, cycloalkylalkyl, aralkyl, heteroaryl-alkyl, hetero-cycloalkyl, heterocycloalkyl-alkyl, bicycloalkyl-alkyl, alkoxyalkyl, alkylthioalkyl, alkylamino-alkyl, fused aryl - cycloalkyl, cycloalkyl, fused aryl -cycloalkyl- alkyl, fused heteroaryl-cycloalkyl, polycycloalkyl, polycycloalkyl - alkyl, fused heteroaryl - cycloalkyl - alkyl, or dialkylaminoalkyl, carboxyalkyl, and alkoxycarbonylalkyl;

Q is selected from the group consisting of

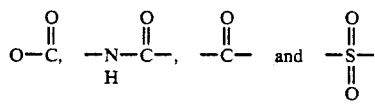

and

M is independently lower alkyl, substituted alkyl, cycloalkyl, substituted cycloalkyl, alkenyl, substituted alkenyl, aryl, substituted aryl, aralkyl, substituted aralkyl, substituted alphatic heterocycle, heteroaryl, heteroaryl-alkyl, heterocyclo-alkylalkyl, heterocycloalkyl, or substituted aromatic heterocycle. The above substituents may optionally be substituted by the following functionalities: hydroxy; amino; alkylamino; dialkylamino; alkanoyl; arylcarbonyl; amido; alkylcarbonylamino; aklylaminocarbonyl; arylcarbonylamino; aryl-alkylcarbonylamino; carboxy; aryloxycarbonyl; aralkoxycarbonyl; alkanoyloxy; aroyloxy; aralkanoyloxy; alkylsulfonamido; cycloalkylsulfonamido; arylalkylsulfonamido; arylsulfonamido; arylsulfonamido; alkoxycarbonyl; and aralkoxycarbonylamino.

In particular, M is preferably selected from one of the following:

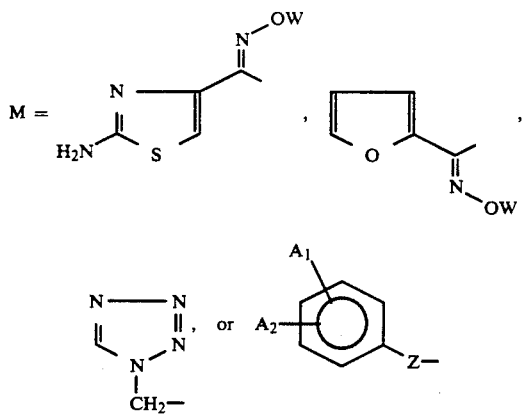

wherein $A_1$ and $A_2$ are each independently hydrogen, lower alkyl, halogen, acetyl, trihaloacetyl, trihalomethyl, alkoxy, nitro, carboxy, alkoxycarbonyl, cyano, sulfonamido, amino alkylamino, dialkylamino, carbonyl, or alkanoyl.

The alkyl groups per se and in the alkyl moiety in aralkyl, cycloalkyl-alkyl, polycycloalkyl-alkyl, heteroaryl-alkyl and the like, and in alkoxy, alkylthio, alkanoyl, carbalkoxy, and alkylamino, may be straight chained or branched and are preferably lower alkyl groups containing from one to ten carbons. Such groups include methyl, ethyl, propyl, isopropyl, butyl, isobutyl, amyl, iso-amyl, hexyl, and the like.

The alkenyl and alkynyl groups may also be branched or straight-chained and contain from two to ten carbon atoms. Such groups include vinyl, ethynyl, propenyl, allyl, isopropenyl, propyl, butynyl, pentynyl, and the like.

In the definition of the X-substituent, cycloalkyl, polycycloalkyl, aryl, heteroaryl, aryalkyl, fused arylcycloalkyl groups and the like may contain from three to twenty-five carbon atoms and may carry substituents such as lower alkyl, alkenyl, alkynyl, hydroxy, thio, amino, alkoxy, alkylthio, alkyl-amino, halogen, acetyl, trifluoroacetyl, and nitro. Examples of such X-substituents include such radicals as cyclopropyl, cyclobutyl, cyclopentyl, cyclohexyl, cycloheptyl, norbornyl, adamantyl, phenyl, tolyl, benzyl, phenethyl, pyridyl, pyridylmethyl, indanyl, imidazolyl, furyl, furfuryl, tetrahydrofurfuryl, benzimidazolyl, morpholinyl, pyrrolylo, pyrrolidyl, piperidyl, piperzinyl, napthyl, dimethoxyphenethyl, dimethoxyphenyl, quinolyl, isoquinolyl, and the like.

In the definition of the X-substituent, wherein X is a heterocyclic group, such group may be mono or polycyclic and include the above groups. The nitrogen in the pyridyl substituent may be oxidized to the N-oxide, and the sulfur in tetrahydrothienyl may be oxidized to the sulfone or sulfoxide.

It is known to those skilled in the art that the N-substituted amides of the present invention may have several asymmetric carbon atoms and thus may exist in several diastereomeric mixtures. The preferred compounds of the present invention are of the S-configuration which corresponds to the L-configuration of naturally occurring alpha amino acids. The methods of synthesis described in Scheme A provides the products as a mixture of diastereomers, based upon the fact that the starting materials are (dl)-mixtures. To those skilled in the art, it is expected that the individual, separated diastereomers may not have the same biologic activity, (e.g. one may be more active than the other). The present invention contemplates all diastereomeric mixtures as well as the active S and R forms.

As will be appreciated by those skilled in the art, the trifluoromethyl ketones and difluoromethyl ketones of the present invention may exist as solvates or in particular hydrates as is represented by the structures IIA, IIB, IIC, IID, IIE, and IIF below. All such hydrates and solvates are within the scope of the present invention.

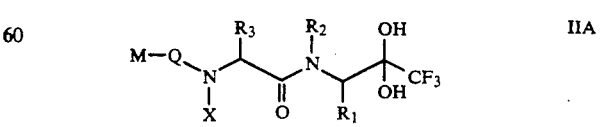

IIA

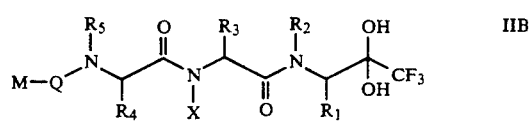

IIB

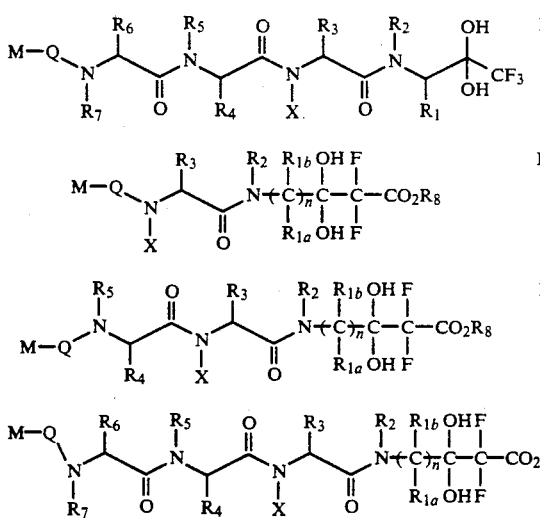

To those skilled in the art it will be appreciated that starting materials for synthesis of the compounds of the present invention are derived from commercially available amino acids, and are obtained from the following: glycine, alanine, valine, leucine, isolleucine, phenylalanine, norleucine, ornithine, tyrosine, tryptophan, glutamine, asparagine, aspartic acid, glutamic acid, lysine, serine, threonine, methionine, sarcosine.

The present invention describes the utilization of non-naturally occurring N-substituted amino acids to obtain potent and specific inhibition of HLE both in vitro and in vivo. Unlike known inhibitors of HLE which embody proline as the penultimate C-terminal residue, the present invention utilizes exclusively non-naturally occurring N-substituted amino acids to obtain potent and specific inhibitors of HLE. This result is surprising and unexpected since it has previously been known that elastase prefers proline as the residue under question.

Scheme A

The non-naturally occurring N-substituted amino acids utilized in the present invention are normally prepared in one of two ways. The first method involves the treatment of an appropriately substituted primary amine 1 with halo-CH($R_3$) COOR$_8$ to give 2.

The second method involves the reductive alkylation of an appropriately substituted ketone or aldehyde 3 with an appropriately substituted alpha-amino acid 4 to give 2. To those skilled in the art it is known that the latter reaction may be accomplished by catalytic hydrogenation or by hydride reduction (eg. NaCNBH$_3$).

The required trifluoromethyl nitro alcohol 6 is conveniently prepared by the treatment of appropriately substituted nitro compounds of formula $R_1CH_2NO_2$ with trifluoroacetaldehyde or trifluoroacetaldehyde ethyl hemiacetal of formula $CF_3CH(OH)OCH_2CH_3$. The trifluoromethyl nitro alcohol 6 is obtained as a mixture of threo and erythro-diastereomers. Normally the diastereomers are separated from one another at this stage by chromatography, crystallization, and/or both. The nitro compound 6 is reduced to the amino trifluoromethyl alcohol 7 by a variety of reducing agents familiar to those skilled in the art (eg. LiAlH$_4$, catalytic hydrogenation, etc.). The amine 7 is normally isolated as its hydrochloride salt and is used directly without further purification.

The non-naturally occurring N-substituted amino acids 2 are condensed with the appropriately substituted N-protected alpha amino acids according to methods commonly used in peptide synthesis by those skilled in the art (eg. M. Bodanszky and A. Bodanszky, "The Practice of Peptide Synthesis", Springer-Verlag, Berlin (1984); M. Bodanszky, "Principles of Peptide Synthesis", Springer-Verlag, Berlin (1984)) to give the non-naturally occurring dipeptide intermediates 8. The intermediate 8 is deprotected to give the acid 8 ($R_8=H$). The acid is condensed by standard methods familiar to those skilled in the art with the amino fluoro alcohol 7 to give 9. The methods of protection and deprotection of amino acids and peptides described in the present invention are well known to those skilled in the art. In the present invention, for example, commonly used protecting groups for nitrogen can be either CBZ or tert-Boc, although others are also contemplated (e.g., FMOC, TROC, etc.). The CBZ intermediates 9 are normally deprotected by catalytic hydrogenolysis whereas the tert-Boc group is removed by acid. Deprotection of the CBZ-intermediate 9 affords the intermediate amines.

The conversion of intermediates 9 into intermediates 10 by their reaction with appropriate reagents for the formation of amides, ureas, urethanes, and sulfonamides including acid chlorides, anhydrides, isocyanates, chloroformates, sulfonyl chlorides is familiar to those skilled in the art. Unless otherwise stated the intermediates 10 are usually obtained as a mixture of diastereomers. All diastereomers are within the scope of this invention.

As well be known to those skilled in the art the exact order of decoupling and condensation need not conform strictly to the order described above and may be altered.

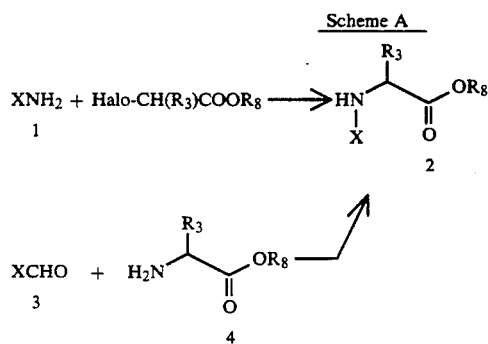

Scheme A

Scheme A

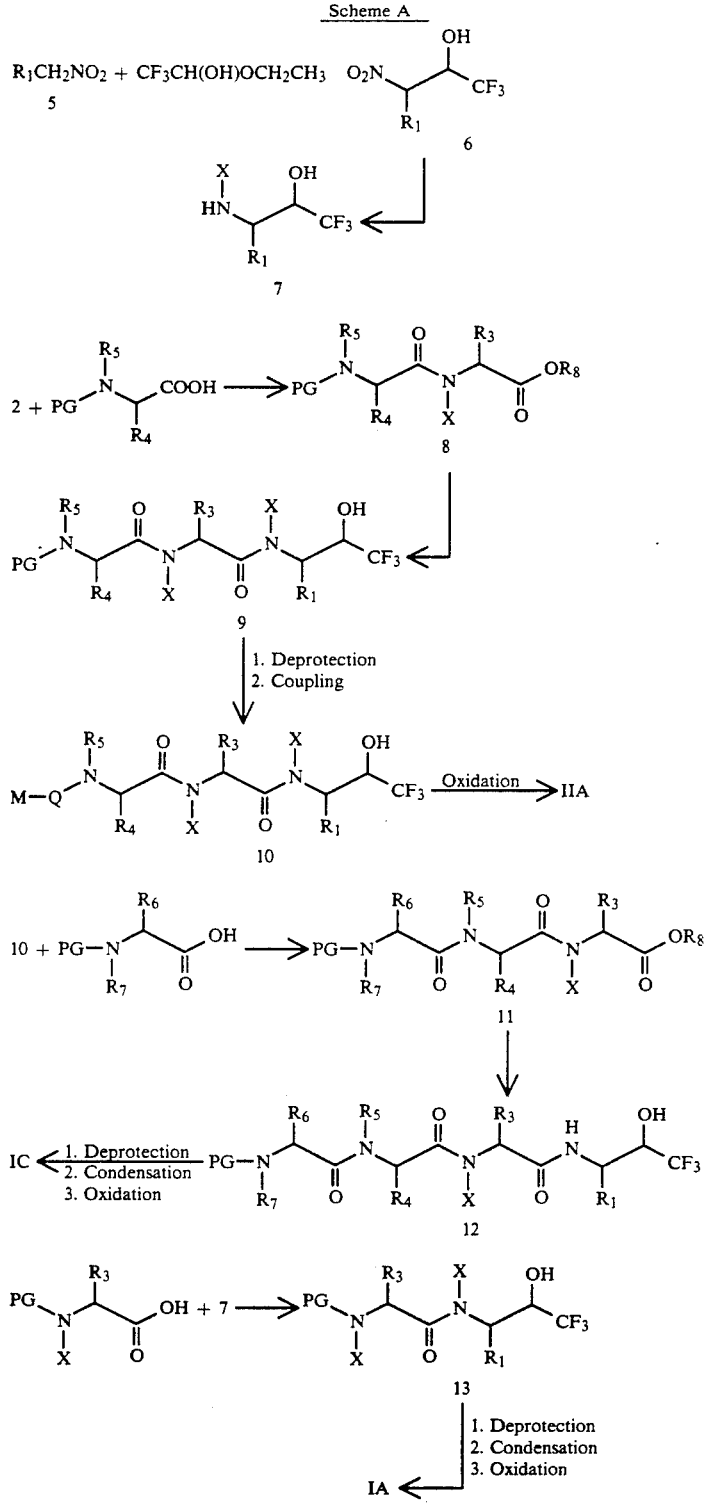

The intermediates 10 are oxidized to provide the products IA by a number of various reagents and conditions familiar to those skilled in the art. For example, the intermediates 10 can be oxidized to the products IA by PCC (pyridinium chlorochromate), PPC (pyridinium dichromate), oxalyl chloride/DMSO, Jones reagent, Collins reagent, etc. However the preferred method of oxidation is by utilization of the Dess-Martin periodane reagent which is commercially available. The utilization of this reagent has previously been described (D.B. Dess et al, *Journal of Organic Chemistry*, 48, 4155 (1983).

To those skilled in the art it will be appreciated that the required trifluromethyl alcohol 7 may also be obtained via the Darkin-West reaction (H.D. Darkin and R. West, *J. Biol. Chem.*, 78, 91,745, and 757 (1928); E.J. Bourne, J. Burdon, V.C.R. McLouglin et al., *J. Chem. Soc.*, 1771 (1961).

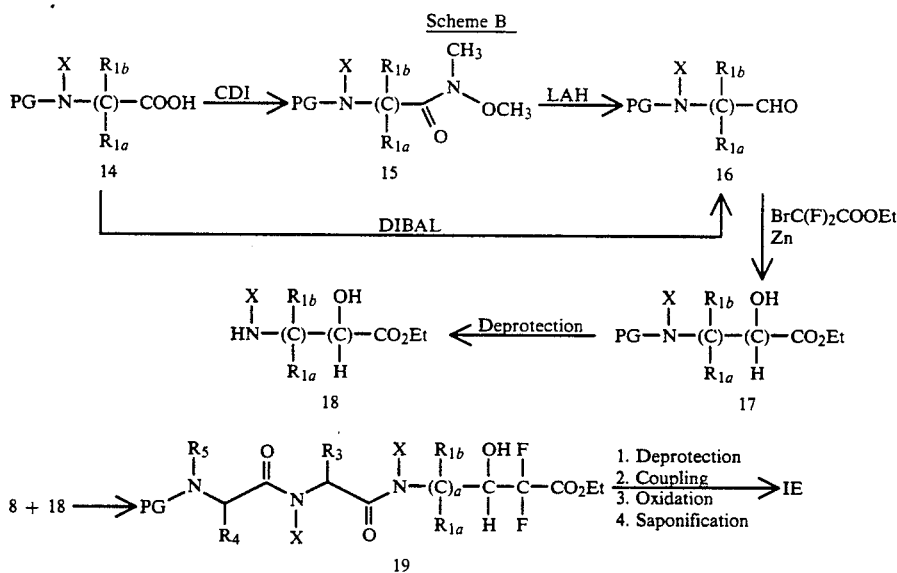

Scheme B

Scheme B

The synthesis of the difluoro products are prepared ideally according to Scheme B. N-protected commercially available alpha-amino acids (preferably tert-Boc) are converted to the amino acid aldehydes 15 by a number of possible means familiar to those skilled in the art. One method involves the direct reduction of the amino acids 14 by known reducing agents (eg. DIBAL, diisobutylaluminum hydride). Alternatively the acids 14 are reduced to the alcohols 15 by known methods and then the alcohols are oxidized to the aldehydes 16 by known methods (eg, Swern oxidation, PCC, etc). The most desirable means of obtaining the aldehydes 16 involves the condensation of acids 14 with HNCH$_3$(OCH$_3$) utilizing CDI (carbonyldiimidazole) as the condensing reagent to give the amides 15. The amides 15 are reduced with LiAlH$_4$ to give the aldehydes 16. The aldehydes 16 are treated under Reformatsky reaction conditions with BrC(F)$_2$COOR$_8$ to give the intermediates 17. The intermediates 17 are then condensed by methods familiar to those skilled in the art with N-substituted non-naturally occurring amino acids 8 (described in Scheme A above) to give the amides 19. The amides 19 are transformed to IE by methods analogous to those described above for Scheme A and familiar to those skilled in the art.

As will be appreciated to those skilled in the art the exact order of the steps described in Scheme B may be altered.

The esters 19 may be saponified to give the corresponding carboxylic acids (R$_8$ is hydrogen).

The compounds of the present invention are potent inhibitors of HLE, as demonstrated in the following tests.

Elastase Inhibition—In Vitro Method

The method of K. Nakajima et al, *Journal of Biological Chemistry*, 254: 4027-4032 was adapted to microtiter format. The in vitro assay is based upon the hydrolysis of the commercially available (Sigma Chemical Company, St. Louis, Missouri) substrate methoxy 0-succinyl-L-alanyl-L-alanyl-L-prolyl-L-valine para-nitroanilide (MeO-Suc-Ala-Sla-Pro-Val-pNA) and the resulting release of p-nitroanilide (pNA), which absorbs at 405 nm.

Equipment
a. Microtiter plates (96 well, flat bottom)
b. Vmax Kinetic Microtiter Plate Reader, equipped with 405 nm filter (Molecular Devices)
c. Microtiter Plate Mixer (Fisher Scientific)
d. Spectrophotomer (e.g., Cary 118; for Ki and Km determinations)

Reagents
a. Human sputum elastase ( HSE ) (Elasten Products Co., Pacific, Mo.) dissolved in 1 mg/mL in 0.05 M sodium chloride and frozen (50 μL aliquots) at −20° C. until used.
b. Stock solution of MeO-Suc-Ala-Ala-Pro-Val-pNA dissolved at 15 mM in dimethylsulfoxide (DMSO) and frozen (4 mL aliquots) at −20° C. until used.
c. Assay buffer: 0.1 M Tris buffer, pH 7.5 containing 0.5 sodium chloride Screening is performed in microtiter plates, using 0.5 mM substrate and monitored on a Microtiter Reader. Enzyme activity (+/− test compound) is determined as the rate of pNA release (linear regression analysis of slope). Inhibitory activity of the test compound is calculated relative to the uninhibited enzyme control, as follows:

$$\% \text{ Inhibition} = 100 - \frac{\text{rate (with test compound)}}{\text{rate (enzyme control)}}$$

A frozen aliquot of HSE is thawed and diluted with assay buffer to a stock concentration of 0.02 mg/mL ( 30×assay concentration). A frozen aliquot of the substrate stock solution is thawed and diluted to 0.5 mM with the assay buffer (final DMSO concentration is 10%). 10 μl of the test compound stock solution (or assay buffer) and 10 μl of the HSE stock solution are pipetted into each microtiter well, in duplicate. The plate is mixed well, and pre-incubated at room temperature for 15 minutes. A 300 μl substrate solution is then added to each well and the OD$_{405}$ is followed for approximately 30 minutes.

Table I sets forth the results of in vitro testing with the compounds of the present invention.

TABLE I
In Vitro Results Of Inhibitors

[Structure: Q-NH-CH(CH(CH3)CH3)-C(O)-N(X)-CH2-C(O)-NH-CH(C(CH3)2-C(O)-CF3)]

| X | Q | IC50 (ug/mL) |
|---|---|---|
| 3,4-Dimethoxyphenethyl | CBZ | 0.432 |
| 2-indanyl | CBZ | 0.21 |
| 3,4-Dimethoxyphenethyl | p-[p-Cl($C_6H_4$)$SO_2$NHCO]($C_6H_4$)CO— | 0.0838 |
| exo-Norbornyl | p-[p-Cl($C_6H_4$)$SO_2$NHCO]($C_6H_4$)CO— | 0.045 |
| Cyclopentyl | CBZ | 0.082 |
| Cyclopentyl | p-[p-Cl($C_6H_4$)$SO_2$NHCO]($C_6H_4$)CO— | 0.066 |
| Cyclopentyl | p-[p-Cl($C_6H_4$)$SO_2$NHCO]($C_6H_4$)CO— | 0.081 |

Thus, the compounds of the present invention have demonstrated potent and specific in vitro inhibitory activity of HLE (of the order, IC50=0.04 to 0108 micromolar) when assayed by the method described above.

Elastase Inhibition—Animal Model

When instilled into the lungs of hamsters, purified preparations of human neutrophil elastase (HNE) will produce an emphysema like state. Acute challenge (18 hours) with 50 μg of HNE results in pulmonary hemorrhage which can be readily quantitated by measuring total RBC's (red blood count) and hemogloblin concentration of lung lavage samples.

HNE (obtained from Elastin Products Co., Pacific, MO) was diluted to 250 μg/mL in 0.9% sterile saline. Syrian Golden Hamsters, males, weighing approximately 90-130 grams, were obtained from Charles River Laboratories. The experiments described below are conducted using at least three animals per group.

Anesthesia required for the intratracheal administration of compounds and elastase was induced by the i.p. injection of Ketamine hydrochloride, 10 mg/100 gram body weight plus Xylazine, 1 mg/100 gram body weight.

Hamsters were anesthetized as described above and the trachea were surgically exposed. Test compounds were administered via 27g needle inserted directly into the trachea in 0.1 mL volume followed by 0.1 mL saline push. Three to five minutes later 50 μg of HNE (0.2 mL) was administered via the same set-up followed by a 0.1 mL saline push. The animals were surgically closed. Eighteen hours later the animals were sacrificed by an overdose of pentobarbitol, whole lung lavage were performed and assayed for hemoglobin concentration and cellular infiltration.

Lung lavage using 8 mL of saline yields 6.5 to 7.5 mL recovery per animal. Samples were mixed by inversion and 6 mL lavage fluid from each animal used for RBC counts performed on a Coulter ZBI.

Samples were concentrated by centrifugation (1500 rpm, 10 minutes) and brought up to 1.0 mL in saline. Homoglobin concentration was determined spectrophotometrically (540 nm) by the cyanmethemoglobin method using 200 μL sample to 2.5 mL cranmethoglobin reagent (Data Medical Associates, Arlington, Tx.).

Table II sets forth the results of in vivo testing with the compounds of the present invention.

TABLE II
In Vivo Activities Of Inhibitors

[Structure: Q-NH-CH(CH(CH3)CH3)-C(O)-N(X)-CH2-C(O)-NH-CH(C(CH3)2-C(O)-CF3)]

| X | Q | % inhib. (20 ug, i.t.) |
|---|---|---|
| Cyclopentyl | p-[p-Cl($C_6H_4$)$SO_2$NHCO]($C_6H_4$)CO— | 99.2 |
| Cyclopentyl | p-[p-Cl($C_6H_4$)$SO_2$NHCO]($C_6H_4$)CO— Diastereomer of above cmpd. | 99.0 |
| 3,4-Dimethoxyphenethyl | p-[p-Cl($C_6H_4$)$SO_2$NHCO]($C_6H_4$)CO— | 90.2 |
| exo-Norbornyl | p-[p-Cl($C_6H_4$)$SO_2$NHCO]($C_6H_4$)CO— | 93.8 |
| 2-indanyl | p-[p-Cl($C_6H_4$)$SO_2$NHCO]($C_6H_4$)CO— | 92 |

The compounds of the present invention are effective elastase inhibitors that significantly prevent or diminish the severity of the enzyme-induced hemorrhage relative to the enzyme alone. In this in vivo model the compounds of the present invention inhibit the hemorrhage due to HLE ( 50 μg, i.t.) in the hamster by over 90% when administered 20 μg, i.t. As such the compounds of the present invention would be useful in the diagnosis and treatment of tissue degenerative diseases such as pulmonary emphysema, rheumatoid arthritis, adult respiratory distress syndrome, otherosclerosis, osteo arthritis, chronic obstructive lung disease, glomerular nephritis, inter alia.

The compounds of the present invention are unique in that they are composed of non-naturally occurring N-substituted alpha-amino acids. The compounds of this invention are very selective for HLE, and in general they do not inhibit other enzymes. By way of example, Table III shows the selectivity of a representative compound of the present invention for inhibition of HLE while not inhibiting other well known endogenous protases An IC50 of 5 or greater is considered inactive.

TABLE III
Demonstration of Selectivity of Inhibitors

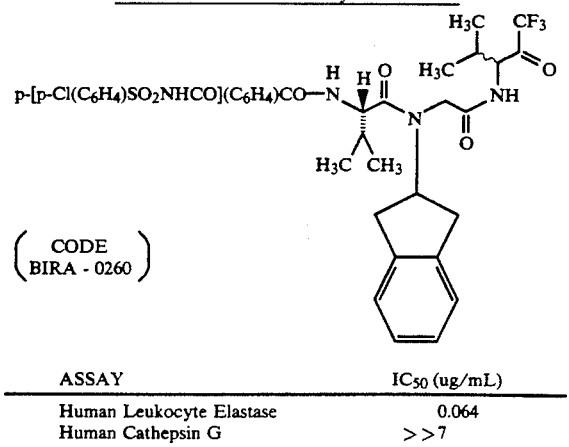

(CODE BIRA - 0260)

| ASSAY | IC50 (ug/mL) |
|---|---|
| Human Leukocyte Elastase | 0.064 |
| Human Cathepsin G | >>7 |

TABLE III-continued

Demonstration of Selectivity of Inhibitors

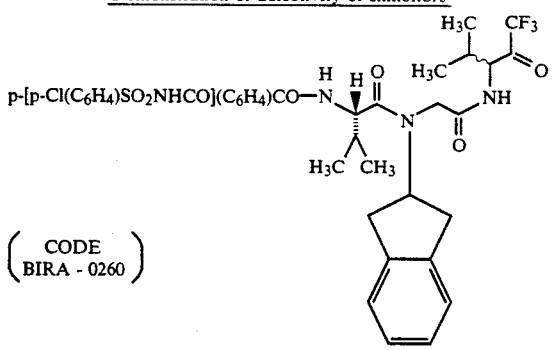

( CODE
BIRA - 0260 )

| ASSAY | IC$_{50}$ (ug/mL) |
|---|---|
| Human Cathepsin B | >5 |
| Recombitant HIV Proteinase | 125 |
| Human Urokinase | >5 |
| Tissue Plasminogen Activator | >5 |
| Human Thrombin | >5 |
| Human C1 Esterase | >>5 |
| Total Complement | >>100 |
| APTT | >>100 |
| PT | >>100 |
| Polio 3C - Proteinase | >63 |
| Human Renin | >5 |

Further, it is known to those skilled in the art that the biological activities of pharmaceutical agents may be diminished in vitro when human serum albumin (HSA) is added. This is due to the probable binding of compounds to protein. In the case of the present invention, however, the compounds of the present invention are just as active in vitro without or with 0.5% HSA and thus would be expected not to bind to plasma protein in an in vivo situation in a diagnostic setting. The results are set forth in Table IV.

TABLE IV

In Vitro Results With Inhibitors - HSA Added

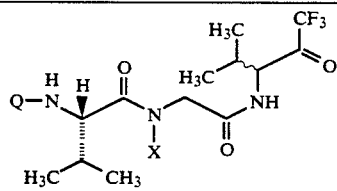

| | | % inhib. (5 ug/mL) | |
|---|---|---|---|
| X | Q | 0% HSA | 0.5% HSA |
| Cyclopentyl | p-[p-Cl(C$_6$H$_4$)SO$_2$NHCO](C$_6$H$_4$)CO— | 100 | 99.8 |
| Cyclopentyl | p-[p-Cl(C$_6$H$_4$)SO$_2$NHCO](C$_6$H$_4$)CO— (Diastereomer of Above) | 99.8 | 99.7 |
| 3,4-Dimethoxyphenethyl | p-[p-Cl(C$_6$H$_4$)SO$_2$NHCO](C$_6$H$_4$)CO— | 98.8 | 96.3 |
| exo-Nornornyl | p-[p-Cl(C$_6$H$_4$)SO$_2$NHCO](C$_6$H$_4$)CO— | 99.8 | 99.5 |
| 2-indanyl | p-[p-Cl(C$_6$H$_4$)SO$_2$NHCO](C$_6$H$_4$)CO— | 99.7 | 99.2 |
| 2-indanyl | CBZ | 98.0 | 98.3 |
| 3,4-Dimethoxyphenethyl | CBZ | 95.1 | 87.8 |
| Cyclopentyl | CBZ | 100 | 99.4 |

Recently, certain trifluoromethyl ketone substituted peptide derivatives have been published which derivatives are stated to be inhibitors of HLE. (EP. Appln. No. 86 300379.4) The compounds in such application are composed exclusively of naturally occurring amino acids at the P$_2$-subsite. In particular, in the above referenced application, proline is utilized exclusively at the P$_2$-subsite since this is the amino acid that appears in elastin, the natural substrate of elastase. In the present invention, however, non-naturally occurring amino acids are utilized at the P$_2$-subsite. It is very unexpected indeed that by utilizing non-naturally occurring amino acid at P$_2$ that both very potent and very specific inhibitors of elastase are afforded as is seen in Tables I and III. Furthermore, what is even more striking and unexpected is the dramatic differences in both potencies and duration when an inhibitor of the present invention containing non-naturally occurring amino acids at P$_2$ is compared to an inhibitor with naturally occurring amino acids. (proline exclusively) at P$_2$, as is reported in EP Appln. No. 86 300379.4. One of the compounds (Code EXRS-0502) reported in EP Appln. No. 86 300379.4 was tested in an acute hemorrhage hamster model (described hereinabove) in a side by side comparison with a representative inhibitor of the present invention (Code BIRA-02601). The structure of BIRA-0260 is given in Table III. The data for this direct side by side comparison is given in two representations: Table V, where absolute values are given and in FIG. 1, which is a bar graph representation. As can be seen from Table V and FIG. 1, the compounds of the present invention, which embody nonnaturally occurring amino acids at P$_2$, have a minimum duration of at least 72 hours, whereas a typical inhibitor of EP Appl. No. 86 300379.4 (Code No. EXRS-0502) has a duration of only approximately 24 hours. As seen from Tables V and FIG. 1, EXRS-0502 does not have significant inhibition at the 48 hour and 72 hour time points whereas BIRA-0260 has very significant inhibition at both 48 hours and 72 hours (61.7% and 48.7% inhibition respectively). Such duration and potencies are unexpected.

TABLE V

In vivo Activities and Duration in the Acute Hamster hemorrhage Model.

| Compound No. | (pretreatment) | Time | Dose % Inhibition | comments |
|---|---|---|---|---|
| BIRA-0260 | 20 ug, i.t. | 72 hours | 48.7 | P< 0.05 |
| | | 48 hours | 63.7 | P< 0.05 |
| | | 24 hours | 96.8 | P< 0.05 |
| EXRS-0502 | 20 ug, i.t. | 72 hours | 10.5 | NS |
| | | 48 hours | 21.5 | NS |
| | | 24 hours | 57.0 | P< 0.05 |

NS = non-significant

The compounds of the present invention may be administered for the alleviation of conditions which include tissue degenerative diseases such as: pulmonary emphysema, arteriosclerosis and osteo- and rheumatoid arthritis, especially emphysema. The mode of administration may be parenteral, oral, intravenous, as a powder or liquid aerosol, or subcutaneous by means of an osmotic pump. For parenteral administration, an intravenous, intramuscular, or subcutaneous injection would be given containing 0.02 to 10 mg/kg of a compound of the present invention two or four times daily. The injection would contain a compound of the invention in an aqueous isotonic sterile solution or optionally a suspension with a preservative such as phenol or a solubilizing agent such as ethylenediamine tetraacetic acid (EDTA). Compounds of the invention may also be administered in a similar manner via a Spinhaler$^{(R)}$ device. Each capsule to be used in the Spinhaler$^{(R)}$ device contains the required amount of a compound of the invention with the remainder of the capsule being a pharmaceutically acceptable carrier. The compounds may also be administered via a liquid aerosol.

Using the schemes and procedures given above, the following additional examples may be prepared.

By following the schemes and procedures described above, the following additional compounds can be prepared.

[[4-(4-Bromophenyl)sulfonylaminocarbonyl]phenyl-1-oxomethyl]-L-valyl-N-(n-hexyl)glycyl-N-[3-(1,1,1-trifluoro-4-methyl-2-oxopentyl)]amide

[[4-(4-Chlorophenyl)sulfonylaminocarbonyl]phenyl-1-oxomethyl ]-L-valyl-N-(phenyl)glycyl-N-[3-(1,1,1-trifluoro-4-methyl-2-oxopentyl)]amide

[[4-(4-Chlorophenyl)sulfonylaminocarbonyl]phenyl-1-oxomethyl ]-L-valyl-N-(4-trifluoromethylphenyl)glycyl-N-[3-(1, 1,1-trifluoro-4-methyl-2-oxopentyl)]amide

[[4-(4-Chlorophenyl)sulfonylaminocarbonyl]phenyl-1-oxomethyl ]-L-valyl-N-(3,4-dimethoxyphenyl)glycyl-N-[3-(1, 1,1-trifluoro-4-methyl-2-oxopentyl)]amide

[[4-(4-Bromophenyl)sulfonylaminocarbonyl]phenyl-1-oxomethyl]-L-(N-methyl) valyl-N-(2,3-dihydro-1H-inden-1-yl) glycyl-N-[3-(1,1,1-trifluoro-4-methyl-2-oxopentyl)]amide

[[4-(4-Chlorophenyl)sulfonylaminocarbonyl]phenyl-1-oxomethyl]-L-valyl-N-[2-(3-indolyl)ethyl]glycyl-N-[3-(1, 1,1-trifluoro-4-methyl-2-oxopentyl)]amide

[[4-(4-Chlorophenyl)sulfonylaminocarbonyl]phenyl-1-oxomethyl ]-L-(N-cyclopentyl)valyl-N-(benzimidazo-2-yl) glycyl-N-[3-(1,1,1-trifluoro-4-methyl-2-oxopentyl)]amide

[[4-(4-Bromophenyl)sulfonylaminocarbonyl]phenyl-1-oxomethyl ]-L-valyl-N-[(N-ethoxycarbonyl)piperidin-4-yl) ]glycyl-N-[3-(1,1,1-trifluoro-4-methyl-2-oxopentyl)]amide [2-Amino-α-(methoxyimino)-4-thiazoleacetyl]-L-valyl-N-(2, 3-dihydro-1H-inden-5-yl)glycyl-N-[3-(1,1,1-trifluoro-4-methyl-2-oxopentyl)]amide

[2-Amino-α-(carboxymethylimino)-4-thiazoleacetyl]-L-valyl-N-(3-thienylmethyl) glycyl-N-[3-(1,1,1-trifluoro-4-methyl-2-oxopentyl)]amide

[2-Amino-α-(methoxyimino)-4-thiazoleacetyl]-L-valyl-N-(benzo thiazole-2-yl)glycyl-N-[3-(1,1,1-trifluoro-4-methyl-2-oxopentyl)]amide

[[4-(4-chlorophenyl)sulfonylaminocarbonyl]phenyl-1-oxomethyl ]-L-valyl-N-[1-[2-(morpholin-4-yl)]ethyl]glycyl-N-[3-(1, 1,1-trifluoro-4-methyl-2-oxopentyl)]amide

[[4-(4-bromophenyl)sulfonylaminocarbonyl]phenyl-1-oxomethyl ]-L-leucyl-N-[1-[2-(pyrid-2-yl)]ethyl]-L-alanyl-N-[3-(1, 1,1-trifluoro-4-m ethyl-2-oxopentyl)-]amide

[2-Amino-α-(methoxyimino)-4-thiazoleacetyl]-L-isoleucyl-N-[1-[2-( 1-methylpyrrolidin-2-yl)]ethyl]glycyl-N-[3-(1, 1,1-trifluoro-4-methyl-2-oxopentyl)]amide

[[4-(4-Bromophenyl)sulfonylaminocarbonyl]phenyl-1-oxomethyl ]-L-valyl-N-(2-indanylmethyl)glycyl-N-[3-(1,1,1-trifluoro-4-methyl-2-oxopentyl)]amide

[[4-(4-Chlorophenyl)sulfonylaminocarbonyl]phenyl-1-oxomethyl ]-L-valyl-N-(piperidin-1-yl)glycyl-N-[3-(1,1,1-trifluoro-4-methyl-2-oxopentyl)]amide

[[4-(4-Chlorophenyl)sulfonylaminocarbonyl]phenyl-1-oxomethyl ]-L-valyl-N-[1-[3-(pyrrolidin-2-one)-1-yl]propyl] glycyl-N-[3-(1,1,1-trifluoro-4-methyl-2-oxopentyl)]amide

[[4-(4-Phenyl)sulfonylaminocarbonyl]phenyl-1-oxomethyl-L-valyl-N-[( tetrahydro-2H-pyran-2-yl)methyl]glycyl-N-[3-(1, 1,1-trifluoro-4-methyl-2-oxopentyl)]amide

[[4-(4-Chlorophenyl)sulfonylaminocarbonyl]phenyl-1-oxomethyl]-L-leucyl-N-( quinuclidin-3-yl)glycyl-N-[3-(1, 1,1-trifluoro-4-methyl-2-oxopentyl)]amide

[2-Amino-α-(methoxyimino)-4-thiazoleacetyl]-L-valyl-N-[1-(3-dimethylamino) propyl]glycyl-N-[3-(1,1,1-trifluoro-4-methyl-2-oxopentyl))amide

[[4-(4-Chlorophenyl)sulfonylaminocarbonyl]phenyl-1-oxomethyl]-L-valyl-N-[(cyclohexyl)methyl]glycyl-N-[3-(1, 1,1-trifluoro-4-methyl- 2-oxopentyl)]amide N-Benzoyl-L-leucyl-N-(4-methoxybut-1-yl)glycyl-N-[3-(1, 1,1-trifluoro-4-methyl-2-oxopentyl)]amide N-Benzyloxycarbonyl-L-leucyl-N-(quinol-1-yl N-oxide)glycyl-N-[3-(1,1,1-trifluoro-4-methyl-2-oxopentyl)]amide

[[4-(4-chlorophenyl)sulfonylaminocarbonyl]phenyl-1-oxomethyl]-L-valyl-N-[(2-pyrrole)methyl]glycyl-N-[3-(1, 1,1-trifluoro-4-methyl-2-oxopentyl)]amide

[[4-(Bromophenyl)sulfonylaminocarbonyl]phenyl-1-oxomethyl ]-L-valyl-N-(5,6-dimethoxy-2,3-dihydro-1H-inden-2-yl) glycyl-N-[3-(1,1,1-trifluoro-4-methyl-2-oxopentyl)]amide

[2-Amino-α-(methoxyimino)-4-thiazoleacetyl]-L-valyl-N-(bicyclo[3. 3.1]nonan-9-yl)glycyl-N-[3-(1,1,1-trifluoro-4-methyl-2-oxopentyl)]amide

[2-Amino-α-(methoxyimino)-4-thiazoleacetyl]-L-valyl-N-(1-adamantyl) glycyl-N-[3-(1,1,1-trifluoro-4-methyl-2-oxopentyl)]amide

[[4-(4-Bromophenyl)sulfonylaminocarbonyl]phenyl-1-oxomethyl ]-L-valyl-N-[L-2-oxohexamethyleneimine-3-yl)]glycyl-N-[3-(1,1,1-trifluoro-4-methyl-2-oxopentyl)]amide

[α-(Methoxyimino)-2-furanacetyl]-L-valyl-N-(propargyl)-glycyl-N-[3-(1,1,1-trifluoro-4-methyl-2-oxopentyl)]amide

[α-(Methoxyimino)-2-furanacetyl]-L-valyl-N-(2-aminoethyl)-glycyl-N-[3-(1,1,1-trifluoro-4-methyl-2-oxopentyl)]amide

[[4-(4-Bromophenyl)sulfonylaminocarbonyl]phenyl-1-oxomethyl ]-L-valyl-N-(6,7,8,9-tetrahydro-5H-benzocyclohepten-7-yl) glycyl-N-[3-(1, 1,1-trifluoro-4-methyl-2-oxopentyl)]amide

[[4-(4-Bromophenyl)sulfonylaminocarbonyl]phenyl-1-oxomethyl ]-L-valyl-N-(5H-benzoimidazol-6-yl)glycyl-N-[3-(1,1,1-trifluoro-4-methyl-2-oxopentyl)]amide

[2-Amino-α-(methoxyimino)-4-thiazoleacetyl]-L-valyl-N-(6, 7-dihydro-5H-cyclopenta[c]pyridin-6-yl)glycyl-N-[-(1, 1,1-trifluoro-4-methyl-2-oxopentyl)]amide

[[4-(4-Chlorophenyl)sulfonylaminocarbonyl]phenyl-1-oxomethyl ]-L-valyl-N-(2,3-dihydro-1H-inden-2-yl)glycyl-N-[3-(1,1,1-trifluoro-4-(3,4-methylenedioxy) phenyl-2-oxobutyl)]amide

[[4-(4-Bromophenyl)sulfonylaminocarbonyl]phenyl-1-oxomethyl) ]-L-valyl-N-(3-carboxypropyl)glycyl-N-[3-(1, 1,1-trifluoro-4-(3,4,5-trimethoxy)phenyl-2-oxobutyl)]amide

[1H-1-Tetrazoleacetyl]-L-valine-N-(benzyl)glycyl-N-[3-(1,1,1 -trifluoro-4-methyl-2-oxopentyl)]amide Using the schemes and procedures outlined hereinabove, the following examples were prepared.

Ethyl N-(cyclopentyl)glycinate.

Cyclopentylamine (85.2 g, 1.0 mol) and triethylamine (101.2 g, 1.0 mol) were dissolved in tetrahydrofuran (750 mL) and cooled to 0°-5° C. by means of an ice-water bath. Ethyl bromoacetate (167 g, 1.0 mol) was added dropwise at 0°-5° C. to the solution. After addition the mixture was allowed to warm up to room temperature and then stirred over night at ambient temperature. The precipitated white triethylamine hydrochloride was filtered off and the filtrate concentrated to an oil which was purified over silica gel using hexane/ethyl acetate (8.2) as the eluent. The collected product was dissolved in ether and cooled by means of an ice water bath. Dry hydrogen chloride was bubbled into the solution whereby the HCL salt of the product precipitated. Filtration yielded 138 g of product as a white solid melting at 174°-176° C.

Analysis calc. for $C_9H_{17}NO_2$ HCl; C, 52.05; H, 8.73; N, 6.74; Cl, 17.07.

Found: C, 52.24; H, 8.85; N, 7.01; Cl, 17.27.

N-CBZ-L-Valyl-N-(cyclopentyl)glycine ethyl ester

CBZ-L-Valine (15.1 g, 0.06 mol) was dissolved in $CH_2Cl_2$ (250 mL) and the following reagents were added in equal molar amounts in the stated order; 4-Dimethylaminopyridine (DMAP), ethyl-N-(cyclopentyl)glycinate and WSCDI. The reaction mixture was allowed to stir at room temperature over night. Evaporation of the solvent yielded a viscous semisolid which was treated with ethyl acetate and then diluted with HCl (4:1) and separated. The organic extract was washed with 1N HCl followed by 5% aqueous $Na_2CO_3$ and saturated aqueous NaCl-solution. After drying over $MgSO_4$, filtration and evaporation under reduced pressure yielded an oil (25.1 g) which was purified over silica gel using $CH_2Cl_2$ as eluent. The product was collected (6.6 g) as a semisolid. (Rf=0.3, silica gel, $CH_2Cl_2:CH_3OH$; 97:3).

N-CBZ-L-Valyl-N-(cyclopentyl)glycine.

N-CBZ-L-Valyl-N-(cyclopentyl)glycine ethyl ester (4.8 g, 0.0119 mol) was dissolved in ethanol (60 mL) and treated with 1N KOH (12.5 mL) in portions of 3 mL. After the mixture was allowed to stir at room temperature over night the ethanol was removed under vacuum, and the residue was treated with water. The residue was extracted three times with ethyl acetate and afterwards the aqueous layer was acidified with dilute HCl. The product was extracted into ethyl acetate and then washed with saturated aqueous sodium chloride. After drying over $MgSO<$, filtration and evaporation under reduced pressure afforded the product as a white semisolid (2.6 g).

exo-N-Bicyclo[2.2.1]hept-2-yl-glycine ethyl ester.

To a solution of exo-2-aminonorborane (15.6 g, 0.14 mol) and triethylamine (14.14 g, 0.14 mol) in acetonitrile (352 mL) was added dropwise ethyl bromoacetate (26.7 g, 0.16 mol) at room temperature. The resulting mixture was allowed to stir over night. The solvent was removed under vacuum and the remaining residue was treated with water and ammonium hydroxide followed by extraction with ethyl acetate. The organic extract was washed consecutively with saturated aqueous solutions of sodium bicarbonate and sodium chloride. The organic extracts were dried over magnesium sulfate and filtered followed by evaporation of the solvent under reduced pressure. The remaining oil was taken up in anhydrous ether (450 mL) and filtered from some insoluble materials. The ether solution was cooled with an ice water bath and the product was isolated as the HCl-salt by the slow addition of ether which was previously saturated with anhydrous hydrogen chloride. Filtration of the product and recrystalization from ethanol/ether (1:5) yielded the desired product (19 g) melting at 195°-197° C. Analysis calc. for $C_{11}H_{19}NO_2xHCl$: C, 56.53; H, 8.62; N, 5.99; Cl, 15.17. Found: C, 56.48; H, 8.68; N, 5.91; Cl, 14.98.

N-CBZ-L-Valyl-N-exo-bicyclo[2.2.1]hept-2-yl-glycine ethyl ester $CH_2Cl_2$ (80 mL) was placed in a reaction flask and consecutively CBZ-L-valine (4.52 g, 0.018 mol), DMAP (2.2g, 0.018 mol), exo-N-bicyclo[2.2.1]hept-2-yl-glycine ethyl ester (4.2g, 0.018 and WSCDI (3.5 g, 0.018 mol) were added. The reaction mixture was allowed to stir for 3 days at room temperature. The $CH_2Cl_2$ was evaporated under vacuum and the residue was treated with ethyl acetate and 1N HCl (4:1). The organic layer was separated and washed with 1N aqueous HCl, followed by 5% aqueous $Na_2CO_3$ and saturated aqueous NaCl. The organic extract was dried over $MgSO_4$ and filtered. After evaporation of solvent under reduced pressure the product was obtained as a crude oil (5.1 g, Rf: 0.7, silica gel, $CH_2Cl_2:CH_3OH$ 97:3) of sufficient purity for saponification.

N-CBZ-L-Valyl-N-(exo-bicyclo[2.2.1]hept-2yl) glycine

N-CBZ-L-Valyl-N-(exo-bicyclo[2.2.1]hept-2-yl)glycine ethyl ester (5.0 g, 0.0116 mol) was dissolved in ethanol (55 mL) and treated with IN KOH (11 mL) in portions. After the mixture was allowed to stir at room temperature over night the ethanol was removed under vacuum, and the residue treated with water. The product was extracted three times with ethyl acetate and afterwards the aqueous layer was acidified with 1N HCL. The product was extracted into ethyl acetate and washed with saturated aqueous sodium chloride. After drying over $MgSO_4$, filtration and evaporation under reduced pressure afforded the product as a white semisolid (2.6 g). Analysis calc. for $C_{22}H_{30}N_2O_5xH_2O$: C, 62.84; H, 7.67; N, 6.66. Found: C, 62.81; H, 7.38; N, 6.64.

Ethyl N-(2-indanyl)glycinate

2-Indanone (25.1 g, 0.19 mol) and glycine ethyl ester hydrochloride (34.5 g, 0.247 mol) were dissolved in absolute ethanol (700 mL) and sodium cyanoborohydride (25.8 g, 0.41 mol) was added in portions to the solution. After addition the mixture was allowed to stir at room temperature over night. The ethanol was removed under reduced pressure and the residue treated with water and extracted into ethyl acetate. The organic extract was repeatedly washed with saturated aqueous solutions of sodium bicarbonate and sodium chloride before being dried over magnesium sulfate and filtered. After the solvent was stripped under vacuum an oil remained which was taken up in ether/ethanol (250/50 mL) and cooled by means of an ice-water bath. Ether previously saturated with anhydrous hydrogen chloride was slowly added to the solution. The precipitated product was filtered off and washed with cold ether/ethanol to yield a white solid (21 g) melting at 166°–168° C.

Analysis calc. for $C_{13}H_{17}NO_2xHCl$: C, 61.05; H, 7.09; N, 5.48; C), 13.86. Found: C, 60.82; H, 7.01; N, 5.33, Cl, 13.98.

N-CBZ-L-Valyl-N-(2-indanyl)glycine ethyl ester

To a solution of CBZ-L-valine (5.0 g, 0.02 mol) in $CH_2Cl_2$ (50 mL) were added 4-dimethylaminopyridine (2.44 g, 0.02 mol), N-(2-indanyl)glycine ethyl ester hydrochloride (5.1 g, 0.02 mol) and 1-(3-dimethylaminopropyl)-3-ethylcarbodiimide hydrochloride (WSCDI), (3.83 g, 0.02 mol). Approximately 20 mL of $CH_2Cl_2$ was used to wash the reagents into the reaction flask. After the mixture was stirred over night the solvent was evaporated off and the residue was treated with ethyl acetate: HCl. The separated organic layer was washed with 1N HCl, 5% aqueous $Na_2CO_3$ and saturated aqueous NaCl -solution followed by drying over magnesium sulfate and filtration. After removal of the solvent under reduced pressure an oil (4.3 g) remained, which was purified over silica gel using $CH_2Cl_2$ as eluent. The titled product (3.4g) was collected as a colorless oil (Rf: 0.7,silica gel, $CH_2Cl_2$: $CH_3OH$ 97:3) and used it as is for saponification.

N-CBZ-L-Valyl-N-2-indanyl glycine

N-CBZ-L-Valyl-N-(2-indanyl)glycine ethyl ester (13.8 g, 0.0305 mol) was dissolved in ethanol (200 mL) and treated with 1N KOH (30 mL) in portions of 5 mL. After the mixture was allowed to stir at room temperature over night the ethanol was removed under vacuum, and the residue treated with water. The aqueous mixture was washed three times with ethyl acetate and the layers separated. The aqueous layer was acidified to pH 3 with 1N HCl. The product was extracted into ethyl acetate and washed with NaCl-solution. After drying over $MgSO_4$, filtration and evaporation under reduced pressure afforded the product as a white semisolid (9.1 g).

Analysis calc. for $C_{24}H_{28}N_2O_5x1/2$ $H_2O$: C, 66.50; H, 6.74; N, 6.46. Found: C, 66.82; H, 6.75; N, 6.17.

Ethyl-N-(3-methylpyridinyl)glycinate

3-Aminomethylpyridine (21.6g, 0.2 mol) and equal molar triethylamine (20.2 g) were dissolved in tetrahydrofuran and cooled by means of an ice water bath to 0°–5° C. Ethyl bromoacetate (33.4 g, 0.2 mol) was added dropwise to the solution where by a suspension formed. The mixture was allowed to stir at room temperature over the weekend. The solvent was concentrated under vacuum. The residue was treated with water and extracted into ethyl acetate. The organic extract was washed repeatedly with water and dried over magnesium sulfate. After filtering from the drying agent the solvent was concentrated and the residue was treated with anhydrous ether. The cloudy solution was filtered through a pad of Celite and afterwards cooled to 0° C. with an ice bath. Slow addition of ether which had previously been saturated with anhydrous hydrogen chloride resulted in the product to precipitate as the HCl-salt. The solid product was filtered and washed with ether to give 15.0 g of a hygroscopic material with a melting point of 125°–127° C.

N-CBZ-Valyl-N-2-(3,4-dimethoxy)phenethyl]glycine ethyl ester.

CBZ-L-Valine (6.3 g, 0.025 mol) was dissolved in $CH_2Cl_2$ (60 mL) and 1,1'-carbonyldiimidazole (CDI) (4.05 g, 0.025 mol) was added in portions. After the mixture had been allowed to stir at room temperature for one hour a suspension of ethyl-N-[2-(3,4-dimethoxyphenethyl]glycinate (8.1 g, 0.0268 mol) and triethylamine (2.7 g, 0.0268 mol) in THF (30 mL) was added. After allowing the stirring of the reaction mixture for three days at ambient temperature the THF was removed under reduced pressure and the residue treated with ethyl acetate: 1N HCl acid (3:1). The organic extract was washed in the following order with 1N HCL, dilute aqueous $Na_2CO_3$ and saturated aqueous NaCl solutions. The organic solution was dried over $MgSO_4$ and filtered followed by evaporation under vacuum to yield an oil ((4.3 g), Rf:0.6, silica gel, $CH_2Cl_2$: $CH_3OH$ 97:3) which was used as is for the next step.

N-CBZ-L-Valyl-N-2-(3,4-dimethoxy)phenethyl glycine

N-CBZ-L-Valyl-N-[2-(3,4-dimethoxy)phenethyl]glycine ethyl ester (9.3 g, 0.0186 mol) was dissolved in ethanol (120 mL) and treated with 1N KOH (20 mL) in portions of 4 mL. After the mixture was allowed to stir at room temperature over night the ethanol was removed under vacuum, and the residue treated with water. The aqueous mixture was washed three times with ethyl acetate and afterwards the aqueous layer was acidified with 1N aqueous HCl. The product was extracted into ethyl acetate and washed with saturated aqueous NaCl. After drying over $MgSO_4$, filtration and evaporation under reduced pressure afforded the product as a white semisolid (6.5 g). The product was purified over silica gel using $CH_2Cl_2$: $CH_3OH$ 97:3 followed by 95:5 as eluent, to afford the pure titled product (3.8g). Analysis calc. for $C_{25}H_{32}N_2O_7x$ 1/2 $H_2O$: C, 62.36; H, 6.91; N, 5.82. Found: C, 62.03; H, 6.74; N, 5.87.

N-CBZ-L-Valyl-N-2-(3,4-dimethoxy)phenethyl]glycyl-N-[3-(1, 1,1-trifluoro-4-methyl-2-hydroxypentyl amide N-CBZ-L-Valyl-N-[2-(3,4-dimethoxy)phenethyl]glycine (2.8 g, 5.925 mmol) was dissolved in THF (45 mL) and 1,1'-carbonyldiimidazole (0.96 g, 5.925 mmol) was added. After two hours of stirring at room temperature a suspension of 3-amino-4-methyl-1,1,1-trifluoro-2-pentanol hydrochloride salt (1.25 g, 6 mmol) and triethylamine (0.61 g, 6 mmol) in THF (10 mL) was added. The mixture was allowed to stir over night and afterwards it was concentrated under vacuum. The remaining residue was treated with ethyl acetate and washed sequencially with 1N HCl, 5% aqueous $Na_2CO_3$ and saturated aqueous sodium chloride. The organic extract was dried over $MgSO_4$, filtered and evaporated to yield a semisolid which was purified over silica gel using $CH_2Cl_2$:$CH_3OH$ 98:2 as eluent. Collected 2.1 g solid melting at 64°–70° C.

Analysis calc. for $C_{31}H_{42}F_3M_3O_7$: C, 59.51; H, 6.77; N, 6.72; F, 9.11. Found: C, 59.49; H, 6.76; N, 6.64; F, 8.72.

2-Methyl-1-nitropropane

1-Iodo-2-methylpropane (92.0 g; 0.5 mole) was dissolved in anhydrous diethyl ether (50 mL) and added dropwise to a precooled (0°–3° C.) suspension of silver nitrite (98.5 g; 0.64 mole) in ether (200 mL). The reaction mixture was protected from light and allowed to stir by means of a mechanical stirrer at room temperature until a negative copper flame rest indicated the completion of the reaction (3–6 days). The mixture was filtered through Celite and the ether was evaporated. The remaining liquid was distilled to yield (38.9 g; 75.5%) of a clear liquid boiling at 55°–60° C. @=50 mm Hg. (Caution: nitro compound°).

Threo-(SS)+(RR)1-4-Methyl-3-nitro-1,1,1-trifluoro-2-pentano 1

2-Methyl-1-nitropropane (38.9 g, 0.377 mole), trifluoroacetaldehyde ethylhemiacetal (60.4 g; @90%, 0.377 mole) and $K_2CO_3$ (2.15 g, 0.0156 mole) were mixed and stirred at 60° C. for 3 hours followed by 3 days at room temperature. A saturated aqueous solution of NaCl (75 mL) was added followed by 1N HCl (50 mL). The organic layers were separated. The aqueous layer was washed twice with 250 mL of ether and the organic layers were combined and washed with a saturated NaCl solution. After drying over $MgSO_4$ and filtration the ether was evaporated under reduced pressure and the residue was placed in a freezer* where the threo-product crystallized. The solid was filtered and washed with cold petroleum ether (bp 37°–50° C.). Yield 21.8g, 28.8%. TLC, Rf=0.62, silica gel, $CH_2Cl_2$: $CH_3OH$ (97:3). The filtrate contains the erythro product isolated as a colorless oil.

*The residue could also be chromatographed over silica gel using a gradient elution of $CH_2Cl_2$:hexane 50:50 to 75:25 to pure $CH_2Cl_2$.

Threo (SS)+(RR)1-3-Amino-4-methyl-1,1,1-trifluoro-2-pentanol hydrochloride

The threo-nitro compound above (21.8 g, 0.108 mole) was dissolved in ether and added dropwise to a suspension of lithium aluminium hydride (13 g, 0.343 mole) under nitrogen. After addition the reaction mixture was allowed to stir at room temperature for 1 hour before the excess $LiAlH_4$ was carefully destroyed with an aqueous saturated solution of potassium bisulfate. The resulting suspension was filtered through Celite and the filtrate was treated with anhydrous ether which was previously saturated with anhydrous hydrogen chloride. After evaporation of the ether a sticky oil remained which upon repeated treatment with ether yielded a white solid (12 g; 0.053 mole, 49%) melting at 123°–125° C.

(Analysis calc. for $C_6H_{11}F_3NO \times HCl$: c: 34.71, H: 6.31, N: 6.75; Found: C: 34.54, H: 6.36, N: 6.71).

Terephthalic acid-di-tert-butyl ester

Terephthaloyl chloride (50.8 g, 0.25 mole) was suspended in tetrahydrofuran (400 mL) and tert-butanol (55.8 g, 0.75 mole) was added followed by pyridine (39.6 g, 0.5 mole). After an initially slightly exothermic reaction the mixture was allowed to stir over night at room temperature. The white solid (pyridinium hydrochloride) was filtered and the filtrate evaporated. The residue was treated with water and the resulting white solid filtered and recrystallized from methanol (hot filtration from insoluble material to yield a white solid.* (54.3g, 78%) mp. 116°–118° C.

*In some experiments a mixture of mono-and di-tert-butyl ester was isolated and used as is for saponification after determining the ratios.

Terephthalic acid-mono-t-butyl ester

A slurry of terephthalic acid di-tert-butyl ester (6.1 g, 0.022 mole) in tert-butanol (30 mL) was added to 1N KOH (22 mL, 0.022 mole). The mixture was heated to 60° C. for 7–8 hours. After cooling the mixture was treated with water and extracted 3 times with ethyl acetate. The aqueous layer was acidified with dilute HCL and the product was extracted into ethyl acetate. After washing of the organic layer with a saturated aqueous NaCl solution and drying over $MgSO_4$, the solvent was filtered and concentrated to yield terephthalic acid mono tert butyl ester as a white solid (4.7 g, 96%) melting at 100°–102° C.

1,1-Dimethylethyl-4-[(4-Chlorophenyl)sulfonylaminocarbonyl] benzoate

The following reaction is conducted under nitrogen utilizing a mechanical stirrer. Terephthalic acid mono-tert-butyl ester (7.7 g, 0.0346 mole) was added to $CH_2Cl_2$ (25 mL) followed by dimethylaminopyridine (4.23 g, 0.0346 mole) and 4-chlorobenzenesulfonamide (6.64 g, 0.0346 moles). In portions WSCDI, 1-(3-dimethylaminopropyl)-3-ethylcarbodiimide hydrochloride (6.64 g, 0.0346 mole) was added and a total of 125 mL $CH_2Cl_2$ was used to wash down the reagent. The reaction was allowed to stir over night at room temperature whereby the suspended solids dissolved. The reaction was evaporated to dryness under reduced pressure and the residue treated with water and ethyl acetate. The organic layer was washed with 20% aqueous citric acid, saturated aqueous $NaHCO_3$ and saturated NaCl. After drying over $MgSO_4$ followed by filtration and evaporation a solid was obtained which was treated with ether and filtered to yield 1,1-dimethylethyl-4-[(4-chlorophenyl)sulfonylaminocarbonyl]benzoate (5.8 g, 42.3%) as a white solid (mp: above 300° C.) which was used for hydrolysis. 4-[(4-Chlorophenyl)sulfonylaminocarbonyl benzene carboxylic acid Trifluoroacetic acid (66 mL) was placed in a flask equipped with a drying tube ($CaCl_2$) and mechanical stirrer. After cooling to 0° C. the tert-butyl ester above from the previous experiment was added in portions. After initially going into solution the reaction mixture formed a heavy white precipitate. After 2 hours of vigorous stirring at 0° C. the mixture was poured onto ice/water and stirred for 2 hours before being filtered, washed with water and dried to yield a white solid. Recrystallization from ethanol/water (1:1) gave the product 4-[(4-Chlorophenyl)sulfonylaminocarbonyl] benzene carboxylic acid in 63% yield melting at 285°–287° C.

N-(tert-butyloxycarbonyl)-L-phenylalanine N,O-dimethylhydroxamide

To a solution of N-t-BOC-L-phenylalanine (53.06, 0.20 mol) in one liter of methylene chloride was added 1,1'-carbonyldiimidazole (38.92g, 0.24 mol). The resulting solution was stirred at room temperature for 3 hours. To this solution was added a mixture of N,O-dimethylhydroxylamine hydrochloride (24.71g, 0.24 mol), triethylamine (24.29g, 0.24 mol) and methylene chloride (100 mL). The resulting mixture was stirred at room temperature for 18 hours. The product solution was then extracted with 1N hydrochloric acid (200ml, 2×100 ml), saturated aqueous sodium bicarbonate (3×200ml) and then saturated aqueous sodium chloride (100ml). The product solution was then dried over MgSO4 and solvent was removed under vacuum to give 70.05g of a white solid.

N-(tert-butyloxycarbonyl)-L-phenylalaninal

A solution of N-(tert-butyloxy-carbonyl)-L-phenylalanine N,O-dimethylhydroxylamide (70.05g, 0.229 mol) in 1400 ml of anhydrous ether was cooled in an ice bath while under a nitrogen atmosphere. To this solution was added lithium aluminum hydride (10.88 g) 0.287 mol) as fast as possible while keeping the reaction under control. The ice bath was removed and the mixture was stirred for 30 minutes where upon it was quenched by addition of 1600 mL of aqueous solution containing 62.11 g of potassium bisulfate. The resulting mixture was stirred for 15 minutes and then was filtered through celite. The phases of the filtrate were separated and the aqueous phase was extracted with ether (2×300ml ). The combined ether layers were then extracted with 1N hydrochloric acid ( 2×1600ml ), saturated aqueous sodium bicarbonate ( 2×1600ml ) and saturated aqueous sodium chloride ( 300mL ). Resulting ether solution was then dried over MgSO4 and solvent was removed under vacuum to give a colorless oil 53.1 g which solidified on standing. The NMR shows about 60% aldehyde. This was used without further purification.

Ethyl 4-[N-(tert-butyloxycarbonyl)amino1-2,2-difluoro-3-hydroxyphe nyl-pentanoate A 3 neck flask was equipped with a condenser, two dropping funnels, a magnetic stirrer and a nitrogen atmosphere. In the flask was placed 24.99g (382 mmoles) of activated zinc (made by stirring zinc dust in 2% hydrochloric acid for ¼ hour, filtering, washing with alcohol, acetone, then ether and drying in vacuum) and 700 mL of anhydrous tetrahydrofuran (dried over sodium/benzophenone and distilled). In one dropping funnel was placed ethyl bromodifluoroacetate (77.61 g, 0.382 mol). In the other was placed N-(tert-butyloxycarbonyl) leucinal 53.1 g, 0.128 mol at 60% purity) and dry tetrahydrofuran (100 mL). The contents of the flask was brought to reflux and the ethyl bromodifluoroacetate was added at a rapid controlled rate followed immediately by the aldehyde solution. The resulting mixture was refluxed for 15 minutes, allowed to cool for 15 minutes and then 150 mL of saturated aqueous sodium chloride and 150 mL of potassium bisulfate were added. The resulting mixture was stirred for 15 minutes and then filtered through celite. The filter cake was washed with ethyl acetate. The combined filtrate was separated by phase. The aqueous phase was extracted with ethyl acetate (2×100 mL). The combined organic layers were then dried over MgSO4 and the solvent was removed under vacuum to give an oil. The oil was put on a silica column and was eluted with 20% ethyl acetate in hexane for a crude separation. Fractions eluting with above solvent were combined and were separated on a Waters Prep 500 HPLC on silica with eluent 20% ethyl acetate in hexane. This yielded 9.60g of the 3(R), 4(S) isomer (mp 116°-126° C.) and 1.60g of the 3(S), 4(S) isomer (mp 105°-109° C.).

N-(tert-butyloxycarbonyl)-L-leucine N,O-dimethylhydroxamide

To a solution of N-(tert-butyloxycarbonyl) leucine (69.4g, 0.3 mol) of methylene chloride (600 mL) was added 1,1'-carbonyldiimidazole (6.86, 0.40 mol). The resulting mixture was stirred at room temperature for 1 hour where upon a mixture of O,N-dimethyl-hydroxylamine hydrochloride (39.02, 0.40 mol) and triethyl amine (40.4 g, 0.4 mol) in methylene chloride (200 mL) was added. The resulting mixture was stirred at room temperature for 5 days. The product solution was washed consecutively with saturated aqueous sodium bicarbonate ( 2×200mL ), water ( 200mL ) and 1N hydrochloric acid ( 2×200mL ). The solution was then dried over MgSO4 and solvent was removed under vacuum to give 61.15 g of a yellow oil. After chromatography on silica with 25% ethyl acetate in hexane as the eluent afforded 29.05 g of pure product as an oil.

Synthesis of N-(tert-butyloxycarbonyl)leucinal

A solution of N-(tert-butyloxycarbonyl)-L-leucine N,O-dimethylhydroxamide (19.80 g, 0.75 mol) in 400 mL was cooled in an ice bath under a nitrogen atmosphere while lithium aluminum hydride (3.58 g, 0.094 mole) was added as rapidly as safely possible. The resulting mixture was stirred for 30 minutes and then the reaction was stopped by addition of a solution of 25.8g of potassium bisulfate in water (400 mL). The mixture was stirred 15 minutes after addition was complete and then was filtered to give a colorless filtrate. The phases were separated. The aqueous layer was extracted with ether (2×100ml). The combined ether layer solution were washed with 1N hydrochloric acid (2×200 mL), saturated aqueous sodium bicarbonate (2×200 mL) and saturated aqueous sodium chloride (100 mL). The resulting ether solution was dried over MgSO4 and the solvent was removed under vacuum to give 13.97g of an oil. NMR indicates purity of aldehyde about 65%. This was used in subsequent reactions without purification.

Ethyl 4-[N-(tert-butyloxycarbonyl)amino)-2,2-difluoro-3-hydroxy-6-methylheptanoate A 3 neck flask was equipped with a magnetic stirrer, 2 dropping funnels, a condenser and a nitrogen atmosphere. In the flask was placed 7.56g (116 mmol) of activated zinc (made by stirring zinc dust in 2% hydrochloric acid for ¼ hour, filtering, washing with alcohol, acetone then ether and drying in vacuum) and 220 mL of anhydrous tetrahydrofuran (dried over sodium/benzophenone and distilled). In one dropping funnel was placed ethyl bromodifluoroacetate (23.62 g, 0.116 mol) and in the other was placed 13.90g (42mmole based on 65% purity) of N-(tert-butyloxycarbonyl) leucinal and anhydrous tetrahydrofuran (30 mL). The contents of the flask was heated to reflux and the ethyl bromodifluoroacetate was added at a rapid controlled rate. This was followed immediately by the addition of the aldehyde solution. The resulting mixture was refluxed an additional 15 minutes and then cooled for 10 minutes. Then a mixture of 75 mL saturated aqueous sodium chloride and 75 ml of IM potassium bisulfate was added. The resulting mixture was stirred for 15 minutes and was filtered through celite. The filter cake was washed with ethyl acetate. The combined filtrate was separated by phase. The aqueous layer was extracted with ethyl acetate (2×50 ml) and the combined organic phases were dried over MgSO$_4$. Solvent was removed under vacuum to give 20.71 g of oil. This product was put on silica column and was eluted with 20% ethyl acetate in hexane for a crude separation. Product containing fractions were chromatographed on a Waters Prep 500 HPLC. The chromatography was done on silica and the eluent was 20% ethyl acetate in hexane. Two isomers were collected: 4.21 g of the 3(R), 4(S) isomer (mp 72°–76° C.) and 0.58 g of the 3(S), 4(S) isomer, and oil. In addition 0.43 g of a mixture of isomers from middle cuts was collected.

L-Valyl-N-[2-(3,4-dimethoxy)phenethyl]glycyl-N-[3-(1, 1,1-trifluoro-4-methyl-2-hydroxypentyl)]amide N-CBZ-L-Valyl-N-[2-(3,4-dimethoxy)phenethyl]glycyl-N-[3-(1, 1,1-trifluoro-4-methyl-2-hydroxypentyl)]amide (1.7g, 2.72 mmol) was dissolved in absolute ethanol (100 mL). Ether which had previously been saturated with anhydrous hydrogen chloride (2.0 mL) and catalytic amounts of palladium on carbon (10 %) were added and the mixture was allowed to shake on a Parr Hydrogenator at 45–50 pounds per square inch hydrogen pressure for several hours. The catalyst was removed by filtration through a bed of Celite. The ethanol was evaporated under reduced pressure to yield the desired product as a semisolid (1.7 g) of sufficient purity for the next reaction.

[4-(4-Chlorophenyl)sulfonylaminocarbonyl phenyl-1-oxomethyl ]-L-Valyl-N-2-(3,4-dimethoxy)phenethyl]-glycyl-N-3-(1, 1,1-trifluoro-4-methyl-2-hydroxypentyl)] amide The following reactants were mixed in the stated order in dry THF (35 mL) at 0°–5° C.: L-Valyl-N-[2-(3,4-dimethoxy)phenethyl]glycyl-N-[3-(1, 1,1-trifluoro-4-methyl-2-hydroxypentyl]amide (0.8 g, 1.63 mmol), hydroxybenzotriazole (HOBT), 0.2 g, 1.48 mmol), 4-[(4-chlorophenyl)-sulfonylaminocarbonyl]benzene carboxylic acid (0.5 g, 1.48 mmol), WSCDI (0.312 g, 1.63 mmol) and triethylamine (0.165 g, 1.63 mmol). The mixture was stirred at 0°–5° C. for 30 minutes and then allowed to warm up to room temperature over a period of four hours. The THF was evaporated under vacuum and the residue treated with ethyl acetate and washed with 1N HCl, 5% aqueous Na$_2$CO$_3$ and saturated aqueous NaCl. The organic extract was dried over MgSO$_4$, filtered and evaporated to dryness (0.9 g). The solid was taken up in minimal amounts of ethyl acetate and treated with diethyl ether whereby the product precipitated as a white solid. Yield: 0.6 g, mp: 166°–176° C. Analysis calc. for C$_{37}$H$_{44}$ClF$_3$N$_4$O$_9$S × ½H$_2$O: C, 54.04; H, 5.52; N, 6.81. Found: C, 53.96; H, 5.27; N, 7.21.

[[4-(4-Chlorophenylsulfonylaminocarbonyl]phenyl-1-oxomethyl]-L-Valyl-N-2-(3, 4-dimethoxy)phenethyl] glycyl-N-[3-(1,1,1-trifluoro-4-methyl-2-oxypentyl)] amide

[[4-(4-Chlorophenyl)sulfonylaminocarbonyl]phenyl-1-oxomethyl ]-L-Valyl-N-[2-(3,4-dimethoxy)phenethyl] glycyl-N-[3-(1,1,1-trifluoro-4-methyl- 2-hydroxypentyl)] amide (0.4 g, 0.492 mmol) was added to THF (20 mL) followed by Dess-Martin periodinane (0.42 g, 0.99 mmol) in CH$_2$Cl$_2$ (30 mL). Trifluoroacetic acid (0.113 g, 0.99 mmol) was slowly added and the reaction mixture was allowed to stir at room temperature over night. The solvents were evaporated off under vacuum and the residue was treated with a mixture of ethyl acetate and saturated aqueous solutions of NaHCO$_3$ and Na$_2$S$_2$O$_3$. The organic layer was separated and washed repeatedly with solutions of dilute aqueous NaHCO$_3$ and Na$_2$S$_2$O$_3$. After a final wash with brine the organic extract was dried over MgSO$_4$, filtered and evaporated to afford a solid, which was purified over silica gel using a gradient elution with CH$_2$Cl$_2$:CH$_3$OH 97:3, 90:10. Yield 0.4 g, mp: 115°–118° C.

Analysis calc. for C$_{37}$H$_{42}$ClF$_3$N$_4$O$_9$S × ½H$_2$O: C, 54.18; H, 5.28; N, 6.83; S, 3.91. Found: C, 54.26; H, 5.22; N, 6.49; S, 3.83.

N-CBZ-L-Valyl-N-(2-indanyl)glycyl-N-[3-(1,1,1-trifluoro-4-methyl-2-hydroxypentyl)1amide N-CBZ-L-Valyl-N-(2-indanyl)glycine (4.25 g, 0.01 mol) was dissolved in CH$_2$Cl$_2$ (60 mL) and 1,1'-carbonyldiimidazole (1.62 g, 0.01 mol) was added. After two hours of stirring at room temperature a suspension of 3-amino-4-methyl-1,1,1-trifluoro-2-pentanol hydrochloride salt (2.1 g, 0.01 mol) and triethylamine (1.01 g, 0.01 mol) in CH$_2$Cl$_2$ ( 30 mL) was added. The mixture was allowed to stir over night and afterwards it was concentrated under vacuum. The remaining residue was treated with ethyl acetate and washed sequencially with 1N HCl, 5% aqueous Na$_2$CO$_3$ and saturated aqueous NaCl solutions. The organic extract was dried over MgSO$_4$, filtered and evaporated to yield an oil which was purified over silica gel using CH$_2$Cl$_2$:CH$_3$OH 97:3 as eluent. Collected 4.5 g of the title compound as a solid melting at 64°–67° C.

Analysis calc. for C$_{30}$H$_{38}$F$_3$N$_3$O$_5$ × ½H$_2$O: C, 61.42; H, 6.70; N, 7.16; F, 9.72. Found: C, 61.35; H, 6.80; N, 7.19; F, 10.10.

L-Valyl-N-(2-indanyl)glycyl-N-3-(1,1,1-trifluoro-4-methyl-2-hydroxypentyl)1amide.

N-CBZ-L-Valyl-N-(2-indanyl)glycyl-N-[3-(1,1,1-trifluoro-4-methyl-2- hydroxypentyl)]amide (1.7 g, 2.94 mmol) was dissolved in absolute ethanol (65 mL). Catalytic amounts of palladium on carbon (10%) was added and the mixture was allowed to shake on a Parr Hydrogenator at 45–50 pounds per square inch hydrogen pressure for several hours. The catalyst was removed by filtration through a pad of Celite. The ethanol was removed under reduced pressure to yield a semisolid (1.3 g) which was used without further purification for the next reaction.

[[4-(4-Chlorophenyl)sulfonylaminocarbonyl phenyl-1-oxomethyl 1-L-Valyl-N-( 2-indanyl)glycyl-N-[3-(1,1,1-trifluoro-4-methyl-2-hydroxypentyl)]amide The following reactants were mixed in the stated order in L-valyl-N-(2-indanyl)glycyl-N-[3-(1,1,1-trifluoro-4-methyl-2-hydroxypentyl)]amide (1.3 g, 2.93 mmol), hydroxybenzotriazole (HOBT), (0.36 g, 2.66 mmol), 4-[(4-chlorophenyl)sulfonylaminocarbonyl]benzene carboxylic acid (0.9 g, 2.64 mmol) and WSCDI (0.56 g, 2.92 mmol). The mixture was stirred at 0°–5° C. for 30 minutes and then allowed to warm up to room temperature over a period of four hours. The THF was evaporated under vacuum and the residue was treated with ethyl acetate and washed with 1N HCl, 5% aqueous Na$_2$CO$_3$ and saturated aqueous NaCl solutions. The organic extract was dried over MgSO$_4$, filtered and evaporated to dryness and the residue was purified over silica gel using CH$_2$Cl$_2$:CH$_3$OH 97:3 as eluent. The collected desired product was as a white solid (1.8 g) melting at 140°–144° C.

Analysis calc. for $C_{36}H_{40}ClF_3N_4O_7S$: C, 56.50; H, 5.27; N, 7.32. Found: C, 56.86; H, 5.54; N, 7.11.

[4-(4-Chlorophenyl)sulfonylaminocarbonyl phenyl-1-oxomethyl ]-L-valyl-N-(2-indanyl)glycyl-N-3-(1,1,1-trifluoro-4-methyl-2-oxypentyl)1amide

[[4-(4-Chlorophenyl)sulfonylaminocarbonyl]phenyl-1-oxomethyl ]-L-valyl-N-(2-indanyl)glycyl-N-[3-(1,1,1-trifluoro-4-methyl-2-hydroxypentyl) ]amide (1.6 g, 2.1 mmol) was added to THF (25 mL) followed by Dess-Martin periodinane (2.66 g, 6.3 mmol) in $CH_2Cl_2$ (45 mL). Trifluoroacetic acid (0.72 g, 6.3 mmol) was slowly added and the reaction mixture was allowed to stir at room temperature over night. The reaction mixture was concentrated under reduced pressure and the residue was treated with a mixture of ethyl acetate and saturated aqueous solutions of $NaHCO_3$ and $Na_2S_2O_3$. The organic layer was separated and washed repeatedly with dilute aqueous solutions of $NaHCO_3$ and $Na_2S_2O_3$. After a final wash with brine the organic extract was dried over $MgSO_4$, filtered and evaporated to afford a solid, which was purified over silica gel using a gradient elution with $CH_2Cl_2CH_3OH$ 97:3, 90:10. Yield 0.9 g, mp: 218°–226° C.

Analysis calc. for $C_{36}H_{38}ClF_3N_4O_7S$: C, 56.65; H, 5.02; N, 7.34; S, 4.20. Found: C, 56.59; H, 5.15; N, 7.08; S, 3.83.

N-CBZ-L-Valyl-N-(exo-bicyclo[2.2.1]hept-2-yl)glycyl-N-[3-(1, 1,1-trifluoro-4-methyl-2-hydroxypentyl)1amide N-CBZ-Valyl-N-(exo-bicyclo[2,2,1]hept-2-yl)glycine (2.3 g, 5.69 mmol) was dissolved in $CH_2Cl_2$ (35 mL) and 1,1'-carbonyldiimiidazole (0.92 g, 5.69 mmol) was added. After stirring for two and a half hours at room temperature a suspension 3-amino-4-methyl-1,1,1-trifluoro-2-pentanol hydrochloride salt (1.2 g, 5.7 mmol) and triethylamine (0.58 g, 5.7 mmol) in $CH_2Cl_2$ (15 mL) was added. The mixture was stirred over night and afterwards it was concentrated under vacuum. The remaining residue was treated with ethyl acetate and washed with 1N HCl, 5% aqueous $Na_2CO_3$ and saturated aqueous NaCl solutions. The organic extract was dried over $MgSO_4$, filtered and evaporated to yield an oil which was purified over silica gel using $CH_2Cl_2:CH_3OH$ 99:1 as eluent. The titled compound was collected as a solid (1.95 g) melting at 59°–65° C. Analysis calc. for $C_{28}H_{40}F_3N_3O_5S \times 5$ $H_2O$: C, 57.72; H, 7.44; N, 7.21. Found: C, 57.53; H, 7.79; N, 7.39.

L-Valyl-N-(exo-bicyclo[2.2.11]hept-2-yl)glycyl-N-[3-(1,1,1-trifluoro-4-methyl-2-hydroxypentyl)]amide N-CBZ-L-Valyl-N-(exo-bicyclo[2.2.1]hept-2-yl)glycyl-N-[3-(1,1, 1-trifluoro-4-methyl-2-hydroxypentyl)]amide (1.4 g, 2.5 mmol) was dissolved in absolute ethanol (60 mL). Catalytic amounts of palladium on carbon (10%) was added and the mixture was allowed to shake on a Parr Hydrogenator at 45-50 pounds per square inch hydrogen pressure for several hours. The catalyst was removed by filtration through a pad of Celite. The ethanol was evaporated under reduced pressure to yield a semisolid (0.8 g) which was used as is for the next reaction.

[4-(4-Chlorophenyl)sulfonylaminocarbonyl]phenyl-1-oxomethyl -L-Valyl-N-(exo-bicyclo2. 2.1]hept-2-yl) glycyl-N-3-(1,1,1-trifluoro-4-methyl-2-hydroxy-pentyl)]amide.

L-Valyl-N-(exo-bicyclo[2.2.1]hept-2-yl)glycyl-N-[3-(1,1,1-trifluoro-4-methyl-2-hydroxypentyl)]amide (0.8 g, 1.9 mmol), HOBT (0.233 g, 1.73 mmol), 4-[(4-chlorophenyl)sulfonyl-aminocarbonyl]benzene carboxylic acid (0.6 g, 1.73 mmol) and WSCDI (0.36 g, 1.9 mmol) were mixed in the stated order in THF (60 mL) at 0°–5° C. The mixture was allowed to stir in the cold for 30 minutes and then allowed to warm up to room temperature over a period of four hours. The THF was evaporated under vacuum and the residue was treated with ethyl acetate and washed with 1N HCl, 5% aqueous $Na_2CO_3$ and saturate aqueous NaCl solutions. The organic extract was dried over $MgSO_4$, filtered and evaporated. The obtained crude product (1.2 g) was purified over silica gel using $CH_2Cl_2:CH_3OH$ 97:3 as eluent. The desired collected product (0.6 g) was used for the next reaction. Analysis calc. for $C_{34}H_{42}ClF_3N_4O_7S \times 2$ $H_2O$: C, 52.40; H, 5.95; N, 7.19. Found: C, 52.54; H, 5.71; N, 7.21.

[[4-(4-Chlorophenyl)sulfonylaminocarbonyl]phenyl-1-oxomethyl ]-L-Valyl-N-(exo-bicyclo[2,2,1]hept-2-yl)-glycyl-N-[3-(1, 1,1-trifluoro-4-methyl-2-oxypentyl)] amide.

[[4-(4-Chlorophenyl)sulfonylaminocarbonyl]phenyl-1-oxomethyl ]-L-valyl-N-( exo-bicyclo[2.2.1]hept-2-yl)-glycyl-N-[3-(1, 1,1-trifluoro-4-methyl-2-hydroxy-pentyl) ]amide (0.6 g, 0.807 mmol) was added to $CH_2Cl_2$ (20 mL) followed by Dess-Martin periodinane (0.69 g, 1.62 mmol). Trifluoro acetic acid (0.18g, 1.62 mmol) was slowly added and the reaction mixture allowed to stir at room temperature over night. The solvents were evaporated off under vacuum and the residue treated with a mixture of ethyl acetate and saturated aqueous solutions of $NaHCO_3$ and $Na_2S_2O_3$. The organic layer was separated and washed repeatedly with solutions of dilute aqueous $NaHCO_3$ and $Na_2S_2O_3$. After a final wash with saturated aqueous NaCl solution the organic extract was dried over $MgSO_4$, filtered and evaporated to a solid. The product was purified over silica gel using a gradient elution with $CH_2Cl_2:CH_3OH$ 97:3, 90:10.

Yield 0.21 g, mp: 234°–239° C.

Analysis calc. for $C_{34}H_{40}ClF_3N_4O_7S$: C, 55.09; H, 5.44; N, 7.56; S, 4.33. Found: C, 54.68; H, 5.50; N, 7.53; S, 4.74.

N-CBZ-L-Valyl-N-cyclopentyl-glycyl-N-[3-(1,1,1-trifluoro-4-ethyl-2-hydroxy-pentyl) ]amide.

N-CBZ-L-Valyl-N-cyclopentyl glycine (2.64 g, 7.0 mmol) was dissolved in $CH_2Cl_2$ (25 mL) and 1,1'-carbonyldiimidazole (1.14 g, 7.0 mmol) was added. After two hours of stirring at room temperature a suspension of 3-amino-4-methyl-1,1,1-trifluoro-2-pentanol hydrochloride salt (1.45 g,7.0 mmol) and triethylamine (0.71 g, 7.0 mmol) in $CH_2Cl_2$ (15 mL) was added. The mixture was allowed to stir over night and afterwards it was concentrated under vacuum. The remaining residue was treated with ethyl acetate and washed sequencially with 1N HCl, 5% aqueous $Na_2CO_3$ and saturated aqueous NaCl solutions. The organic extract was dried over $MgSO_4$, filtered and evaporated to yield an oil which was purified over silica gel using CH$_2$Cl$_2$:CH$_3$OH 99:1 Collected 2.55 g solid melting at 49°–54° C.

Analysis calc. for C$_{26}$H$_{38}$F$_3$N$_3$O$_5$×½ H$_2$O: C, 57.98; H, 7.30; N, 7.80. Found: C, 58.03; H, 7.12; N, 7.70.

L-Valyl-N-cyclopentyl-glycyl-N-3-(1,1,1-trifluoro-4-methyl-2-hydroxypentyl) 1amide N-CBZ-L-Valyl-N-cyclopentyl-glycyl-N-[3-(1,1,1-trifluoro-4-m-ethyl-2-hydroxy-pentyl) ]amide (2.15g, 4.06 mmol) was dissolved in absolute ethanol (85 mL). Etheric HCl (2.0 mL) and catalytic amounts of palladium on carbon (10%) were added. The mixture was allowed to shake on a Parr Hydrogenator at 45–50 pounds per square inch hydrogen pressure for several hours. Filtered the mixture through a pad of Celite and evaporated the ethanol under reduced pressure to yield 1.8 g solid melting at 98°–101° C. Used as is for next reaction.

N-CBZ-L-Valyl-N-(benzyl)glycine ethyl ester

CBZ-L-Valine (12.6g, 0.05mol) was dissolved in CH$_2$Cl$_2$ (250mL) and the following reagents were added in equal molar amounts in the stated order; 4-Dimethylaminopyridine (DMAP), ethyl-N-(benzyl)-glycinate and WSCDI. The reaction mixture was allowed to stir at room temperature over night. Evaporation of the solvent yielded a viscous semisolid which was treated with ethyl acetate and then IN HCl and separated. The organic extract was washed with 1N HCl followed by 5% aqueous Na$_2$CO$_3$ and saturated aqueous NaCl-solution. After drying over MgSO$_4$, filtration and evaporation under reduced pressure afforded an oil (17.6 g) which ws used as is for saponification.

N-CBZ-L-Valyl-N-(benzyl)glycine

N-CBZ-L-Valyl-N-(benzyl)glycine ethyl ester (17.3 g, 0.0406mol) was dissolved in ethanol (200 mL) and treated with 1N KOH (45 mL) in portions of 8.0 mL at 0–5C. The mixture was allowed to stir at room temperature over night. The ethanol was removed under reduced pressure, and the residue was treated with water. Extracted three times with ethyl acetate and afterwards the aqueous layer was acidified with 2N HCl. The product was extracted into ethyl acetate and washed with saturated aqueous sodium chloride. After drying over MgSO$_4$, filtration and evaporation under reduced pressure afforded the product as a white semisolid (14.1 g) melting at 41°–45° C.

Analysis calc. for C$_{22}$H$_{26}$N$_2$O$_5$ : C, 66.32; H, 6.58; N, 7.03. Found: C, 66.25; H, 6.90; N, 6.88.

[[4-(4-Chlorophenyl)sulfonylaminocarbonyl phenyl-1-oxomethyl ]-L-Valyl-N-(cyclopentyl)glycyl-N-[3-(1,1,1-trifluoro-4-methyl-2-hydroxypentyl)amide]

The following reactants were mixed in the stated order in dry THF (35 mL) at 0°–5° C:L-Valyl-N-(cyclopentyl)glycyl-N-[3-(1, 1,1-trifluoro-4- methyl-2-hydroxypentyl)amide (1.0 g, 2.5 mmol), HOBT (0.31g, 2.3 mmol), 4-[(4-chlorophenyl) sulfonyl-aminocarbonyl]benzene carboxylic acid (0.78g, 2.3 mmol), triethylamine (0.25 g, 2.5 mmol) and WSCDI (0.48g, 2.5 mmol). The mixture was stirred at 0°–5° C. for 30 minutes and then allowed to warm up to room temperature over a period of four hours. The THF was evaporated under vacuum and the residue treated with ethyl acetate and washed with 1N HCl, 5% aqueous Na$_2$CO$_3$ and saturated aqueous NaCl. The organic extract was dried over MgSO$_4$, filtered and evaporated to dryness. The white residue was treated with ether/petroleum ether. Filtration afforded (1.1 g) the titled compound as a white solid melting at 171°–175° C. Analysis calc. for C$_{32}$H$_{40}$ClF$_3$N$_4$O$_7$S×½H$_2$O: C, 52.93; H, 5.69; N, 7.71; S, 4.42. Found: C, 52.62; H, 5.38; N, 8.00; S, 4.52.

(4-(4-Chlorophenyl)sulfonylaminocarbonyl phenyl-1-oxomethyl ]-L-Valyl-N-cyclopentyl-glycyl-N-[3-(1,1,1-trifluoro-4-methyl-2-oxypentyl)1amide

[[4-(4-Chlorophenyl)sulfonylaminocarbonyl]phenyl-1-oxomethyl ]-L-Valyl-N-(cyclopentyl)glycyl-N-[3-(1,1,1-trifluoro-4-methyl-2-hydroxy pentyl)]amide (0.72 g, 1.0 mmol) was added to THF (20 mL) followed by Dess-Martin periodinane (1.27 g, 3.0 mmol) in CH$_2$Cl$_2$ (25 mL). Trifluoro acetic acid (0.34g, 3.0 mmol) was slowly added and the reaction mixture allowed to stir at room temperature over night. The solvents were evaporated off under vacuum and the residue treated with a mixture of ethyl acetate and saturated aqueous solutions of NaHCO$_3$ and Na$_2$S$_2$O$_3$. The organic layer was separated and washed repeatedly with solutions of dilute aqueous NaHCO$_3$ and Na$_2$S$_2$O$_3$. After a final wash with brine the organic extract was dried over MgSO$_4$, filtered and evaporated to afford a solid, which was treated with ether. The white precipitate was filtered off (0.42 g, mp: 171°–175° C.) I. The ether filtrate was evaporated and the residue treated with petrol ether/ether. The solid was filtered off (0.18g, mp: 136°–140° C.) II. The two different solids collected are two different diastereomers. Analysis calc. for I, for C$_{32}$H$_{38}$ClF$_3$N$_4$O$_7$S x½ H$_2$O: C, 53.07; H, 5.43; N, 7.74; S, 4.43. Found: C, 52.96;H, 5.18; N, 7.96; S, 4.03.

Analysis calc. for II, for C$_{32}$H$_{38}$ClF$_3$N$_4$O$_7$S ×H$_2$O: C, 52.42; H, 5.50; N, 7.64; S, 4.37. Found: C, 52.46; H, 5.53; N, 7.83; S, 4.49.

N-CBZ-L-Valyl-N-(3-methylpyridinyl)glycine ethyl ester

CBZ-L-Valine (15.4 g, 0.0612 mol) was dissolved in CH$_2$Cl$_2$ (300 mL) and the following reagents were added in equal molar amounts in the stated order; 4-dimethylaminopyridine (DMAP), ethyl-N-(3-methylpyridinyl)glycinate and WSCDI. The reaction mixture was allowed to stir at room temperature over night. Evaporation of the solvent yielded a viscous semisolid which was treated with ethyl acetate and then with water and separated. The organic extract was washed with water followed by 5% aqueous Na$_2$CO$_3$ and saturated aqueous NaCl-solution. After drying over MgSO$_4$, filtration and evaporation under reduced pressure yielded an oil (11.1 g) which was purified over silica gel using CH$_2$Cl$_2$: CH$_3$OH 97.3 as eluent. Isolated 9.2 g of an amber oil.

Analysis calc. for C$_{23}$H$_{29}$N$_3$O$_5$: C, 64.62; H, 6.84; N, 9.83. Found: C, 65.02; H, 6.82 N, 9.92.

N-CBZ-L-Valyl-N-(cycloheptyl)glycine ethyl ester

CBZ-L-Valine (10.05 g, 0.04 mol) was dissolved in CH$_2$Cl$_2$ (300 mL) and the following reagents were added in equal molar amounts in the stated order: 4-Dimethylaminopyridine, ethyl-N-(cycloheptyl)glycinate and WSCDI. Used additional 100 mL CH$_2$Cl$_2$ to wash down the reagents. The reaction mixture was allowed to stir at room temperature over night. Evaporation of the solvent yielded a viscous semisolid which was treated with ethyl acetate and then 1N HCl and separated. The organic extract was washed with 1N HCl followed by 5% aqueous Na₂CO₃ and saturated aqueous NaCl-solution. After drying over MgSO₄, filtration and evaporation under reduced pressure yielded the titled compound as an oil (11.2 g) which was used as is for saponification.

N-CBZ-L-Valyl-N-(cycloheptyl)glycine

N-CBZ-L-Valyl-N-(cycloheptyl)glycine ethyl ester (11.2 g, 0.0259 mol) was dissolved in ethanol (300 mL) and treated with 1N KOH (27 mL) in portions of 5.0 mL at 0°-5° C. After the mixture was allowed to stir at room temperature over night the ethanol was removed under vacuum, and the residue treated with water. The residue was extracted three times with ethyl acetate and afterwards the aqueous layer was acidified with 2N HCl. The product was extracted into ethyl acetate and washed with saturated aqueous sodium chloride. After drying over MgSO₄, filtration and evaporation under reduced pressure isolated the product as a white semisolid (6.5 g) melting at 48°-51° C.

Analysis calc. for $C_{22}H_{32}N_2O_5$: C, 65.32; H, 7.97; N, 6.93. Found: C, 65.02; H, 8.31; N, 6.73.

Ethyl-N-furfurylglycinate

Furfurylamine (48.6 g, 0.5 mol) and triethylamine (50.6 g, 0.5 mol) were dissolved in tetrahydrofuran (1000 mL) and cooled to 0°-5° C. with an ice water bath. Ethyl chloroacetate (61.3 g, 0.5 mol) was dropwise added at 0°-5° C. to the solution. After addition the mixture was allowed to warm up to room temperature and then stirred over night. The precipitated white triethylamine hydrochloride was filtered off and the filtrate concentrated to an oil which was dissolved in ether and cooled by means of an ice water bath. Ether which has been saturated with dry hydrogen chloride was added to the solution whereby the HCl salt of the product precipitated first as a sticky semisolid. Repeated treatment with anhydrous ether afforded the desired product. Filtration yielded 48.4 g product as an amber solid. Used as is for further synthesis.

N-CBZ-L-Valyl-N-(furfuryl)glycine ethyl ester

CBZ-L-Valine (15.4 g, 0.0612 mol) was dissolved in THF (350 mL) and the following reagents were added in equal molar amounts in the stated order; 4-dimethylaminopyridine, ethyl N-(furfuryl)glycinate and WSCDI. The reaction mixture was allowed to stir at room temperature over night. Evaporation of the solvent yielded a viscous semisolid which was treated with ethyl acetate and then 1N HCl and separated. The organic extract was washed with 1N HCl followed by 5% aqueous Na₂CO₃ and saturated aqueous NaCl-solution. After drying over MgSO₄, filtration and evaporation under reduced pressure obtained an oil (25.1 g) which was treated with ether whereby a white precipitate formed. The white solid product (2.8 g, mp: 164°-166° C.) was collected by filtration.

N-(Benzyl)glycine ethyl ester

In a 3 liter erlenmeyer flask was placed 107.2 g (1.0 mole) of benzylamine, 152.0 g (1.5 mole) of triethylamine and 1.5 liter of methylene chloride. The resulting solution was stirred while 167.0 g (1.0 mole) of ethyl bromoacetate was added dropwise. The mixture was washed with water (3×300 mL), dried over magnesium sulfate, filtered and solvent was removed by rotary evaporation. The resulting oil was dissolved in ether and hydrogen chloride saturated ether was then added slowly until precipitation was complete. The precipitate was a gummy solid and the mixture was stoppered and let sit for one day. Over this time the precipitate formed a hard solid which was filtered off and dried in vacuum to give 62.8 g (28%) of N-benzylglycine ethyl ester hydrochloride.

N(Cycloheptyl)glycine ethyl ester

In a 2 liter erlenmeyer flask was placed 49.8 g (0.44 mole) of cycloheptylamine, 66.6 g (0.66 mole) of triethylamine and 1 liter of methylene chloride. The resulting solution was stirred, while 73.4 g (0.44 mole) of ethyl bromoacetate was added dropwise. The mixture was stirred for 16 hours at room temperature and then filtered. The filtrate was washed with water (3×200 mL), dried over magnesium sulfate, filtered and solvent was removed by rotary evaporation. The resulting oil was run through a short column with the eluent being first methylene chloride and then methylene chloride containing 0.25% ammonium hydroxide and 2.5% methanol. A small amount of a fast moving impurity was separated from the bulk of the product. Solvent was again removed from the product by rotary evaporation and the resulting oil was dissolved in ether, dried over magnesium sulfate and filtered. Hydrogen chloride saturated ether was then added to the filtrate and the resulting precipitate was filtered off and dried in vacuum to give 47.8 g (47%) of N-cycloheptylglycine ethyl ester hydrochloride.

What is claimed is:
1. A compound

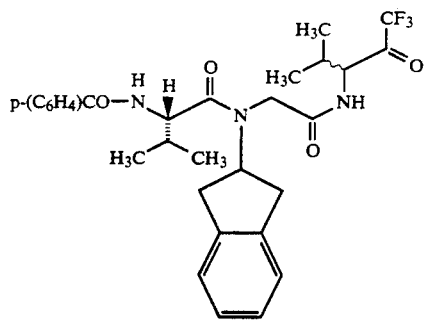

2. A pharmaceutical composition of matter comprising a compound as recited in claim
3. A method for inhibiting hydrolysis of elastin in a warm-blooded animal which comprises administering to said animal a therapeutically effective amount of a compound as recited in claim 1.

* * * * *